United States Patent

Kawamura et al.

[11] Patent Number: 5,837,166
[45] Date of Patent: Nov. 17, 1998

[54] ORGANIC ELECTROLUMINESCENCE DEVICE AND ARYLENEDIAMINE DERIVATIVE

[75] Inventors: Hisayuki Kawamura; Chishio Hosokawa; Tadashi Kusumoto; Hiroaki Nakamura, all of Sodegaura, Japan

[73] Assignee: Idemitsu Kosan Co., Ltd., Tokyo, Japan

[21] Appl. No.: 615,281

[22] PCT Filed: Sep. 28, 1994

[86] PCT No.: PCT/JP94/01585

§ 371 Date: Mar. 27, 1996

§ 102(e) Date: Mar. 27, 1996

[87] PCT Pub. No.: WO95/09147

PCT Pub. Date: Apr. 6, 1995

[30] Foreign Application Priority Data

Sep. 29, 1993 [JP] Japan .................................. 5-243024

[51] Int. Cl.$^6$ .............................. G02F 1/00; C09K 11/06; C07C 211/00

[52] U.S. Cl. ..................... 252/583; 252/301.16; 428/917; 564/307; 564/434

[58] Field of Search ............................... 252/583, 301.16, 252/500; 428/917; 564/307, 434

*Primary Examiner*—Philip Tucker
*Attorney, Agent, or Firm*—Oblon, Spivak, McClelland, Maier & Neustadt, P.C.

[57] ABSTRACT

Organic electroluminescence devices having the life of light emission superior to those of conventional electroluminescence devices, and novel arylenediamine derivatives which can remarkably improve the life of light emission of an organic electroluminescence device when the derivatives are used as a component of the device, are disclosed.

The organic electroluminescence devices of the present invention at least contain a p-phenylenediamine derivative having 6 or more benzene ring skeletons, or at least a 4,4'-biphenylenediamine derivative having 5 biphenyl groups.

The arylenediamine derivatives of the present invention include p-phenylenediamine derivatives having 4 biphenyl groups and 4,4'-biphenylenediamine derivatives having 5 biphenyl groups.

9 Claims, 6 Drawing Sheets

ORGANIC ELECTROLUMINESCENCE DEVICE AND ARYLENEDIAMINE DERIVATIVE

This application is a 371 of PCT/JP94/01585 filed Sep. 28, 1994.

TECHNICAL FIELD

The present invention relates to electroluminescence devices (hereinafter, referred to as organic EL devices) and novel arylenediamine derivatives. More particularly, the present invention relates to organic EL devices having a remarkably improved life of light emission by using an arylenediamine derivative as a component thereof, particularly as a material of a hole transporting layer thereof, and novel p-phenylenediamine derivatives and 4,4'-biphenylenediamine derivatives which can remarkably improve the life of light emission of organic EL devices.

BACKGROUND ART

As for the construction of organic EL devices, various types have heretofore been known. It has been disclosed that an aromatic tertiary amine is used as the material of a hole transporting layer in an organic EL device having the construction of ITO (Indium Tin Oxide)/a hole transporting layer/a light emitting layer/a cathode (Japanese Patent Application Laid-Open No. Showa 63(1988)-295695), and a high luminance of several hundred cd/m$^2$ with an applied voltage of 20 V or more has been enabled by the device having this construction. Furthermore, it has been disclosed that, by using TPD [N,N'-diphenyl-N,N'-bis(3-methylphenyl)-1,1'-biphenyl-4,4'-diamine] as the aromatic tertiary amine, a luminance of 100 cd/m$^2$ can be obtained with an applied voltage of 8 V even in the case of blue light emission (Japanese Patent Application Laid-Open No. Heisei 3(1991)-231970). However, the above-disclosed diamine derivative has a drawback in that contribution of canonical forms is weak because the two amino groups are located at positions separate from each other, and the diamine derivative has a high ionization potential. Therefore, the driving voltage of the EL device cannot be sufficiently decreased, and the device furthermore has a half-life period of several ten hours. Thus, the device described above does not have a sufficient property for practical application.

A compound derived by using m-phenylenediamine as the diamine has been disclosed (Japanese Patent Application Laid-Open No. Heisei 5(1993)-105647). A sufficient electron-donating property can be expected from this compound because only a phenylene group is present between the two amino groups. However, this compound has a drawback in that this compound has a still higher ionization potential than those of the diamine derivatives described above because the m-phenylenediamine skeleton in this compound cannot have canonical forms, the driving voltage of the EL device therefore cannot be sufficiently decreased, and the life of light emission is short.

When application of an EL device to a flat panel display or the like is considered, it is necessary that the life of light emission be improved. It has been disclosed in Japanese Patent Application Laid-Open No. Heisei 5(1993)-107758 that a triamine compound can be used as a material of charge transport in an EL device. However, this compound cannot sufficiently satisfy the requirements described above.

DISCLOSURE OF THE INVENTION

Under the situation described above, the present invention has an object of providing an organic EL device having a decreased driving voltage or an organic EL device having a remarkably improved life of light emission.

As the result of extensive studies undertaken by the present inventors to develop the organic EL device having the desirable properties described above, it has been discovered that an organic EL device having a long life of light emission can be obtained by using an arylenediamine derivative having a specific structure as a component of an organic EL device, particularly as a material of a hole transporting layer.

It has also been discovered by the present inventors that, among the arylenediamine derivatives described above, compounds having some types of structure, p-phenylenediamine derivatives having specific structures, and 4,4'-biphenylenediamine having specific structures are novel compounds which are not described in literature, and that an organic EL device having a remarkably improved life of light emission can be obtained by using these compounds as a component of an organic EL device, particularly as a material of a hole transporting layer. The present invention has been completed on the basis of the above discoveries.

Thus, the present invention provides:

(1) An organic electroluminescence device at least containing a p-phenylenediamine derivative having 6 or more benzene ring skeletons which is represented by the general formula (I):

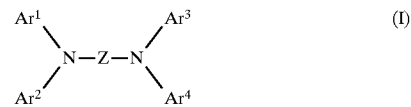

wherein Z represents p-phenylene group; $Ar^1$, $Ar^2$, $Ar^3$, and $Ar^4$ represent each an aryl group having 6 to 20 carbon atoms, and may be the same with each other or different from each other; Z, $Ar^1$, $Ar^2$, $Ar^3$, and $Ar^4$ may each be substituted with alkyl groups having 1 to 6 carbon atoms, alkoxy groups having 1 to 6 carbon atoms, or phenyl groups; and the combination of $Ar^1$, $Ar^2$, $Ar^3$, $Ar^4$, and Z of the central skeleton must have 6 or more benzene ring skeletons;

(2) A p-phenylenediamine derivative represented by the general formula (II):

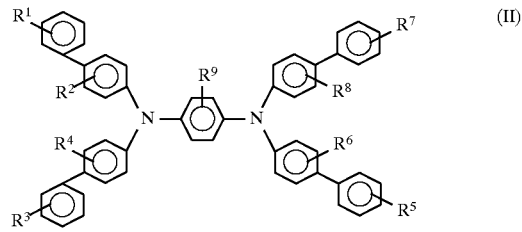

wherein $R^1$ to $R^9$ represent each a hydrogen atom, an alkyl group having 1 to 6 carbon atoms, an alkoxy group having 1 to 6 carbon atoms, or a phenyl group, and may be the same with each other or different from each other; and $R^1$ and $R^2$, $R^2$ and $R^4$, $R^3$ and $R^4$, $R^5$ and $R^6$, $R^6$ and $R^8$, $R^7$ and $R^8$, $R^2$ and $R^9$, $R^4$ and $R^9$, $R^6$ and $R^9$, and $R^8$ and $R^9$, may each form a ring by being bonded to each other;

(3) An organic electroluminescence device at least containing a p-phenylenediamine derivative represented by the general formula (II);

(4) A 4,4'-biphenylenediamine derivative represented by the general formula (III):

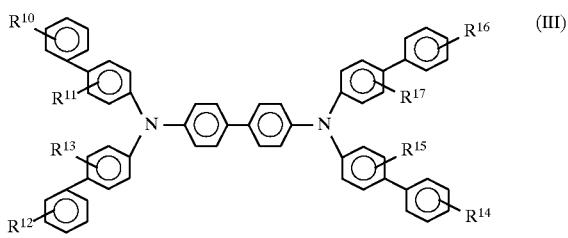

wherein $R^{10}$ to $R^{17}$ represent each a hydrogen atom, an alkyl group having 1 to 6 carbon atoms, an alkoxy group having 1 to 6 carbon atoms, or a phenyl group, and may be the same with each other or different from each other; and $R^{10}$ and $R^{11}$, $R^{11}$ and $R^{12}$, $R^{12}$ and $R^{13}$, $R^{14}$ and $R^{15}$, $R^{15}$ and $R^{17}$, and $R^{16}$ and $R^{17}$, may each form a ring by being bonded to each other; and (5) An organic electroluminescence device at least containing a 4,4'-biphenylenediamine derivative represented by the general formula (III).

THE MOST PREFERRED EMBODIMENT TO CARRY OUT THE INVENTION

Figure 1:
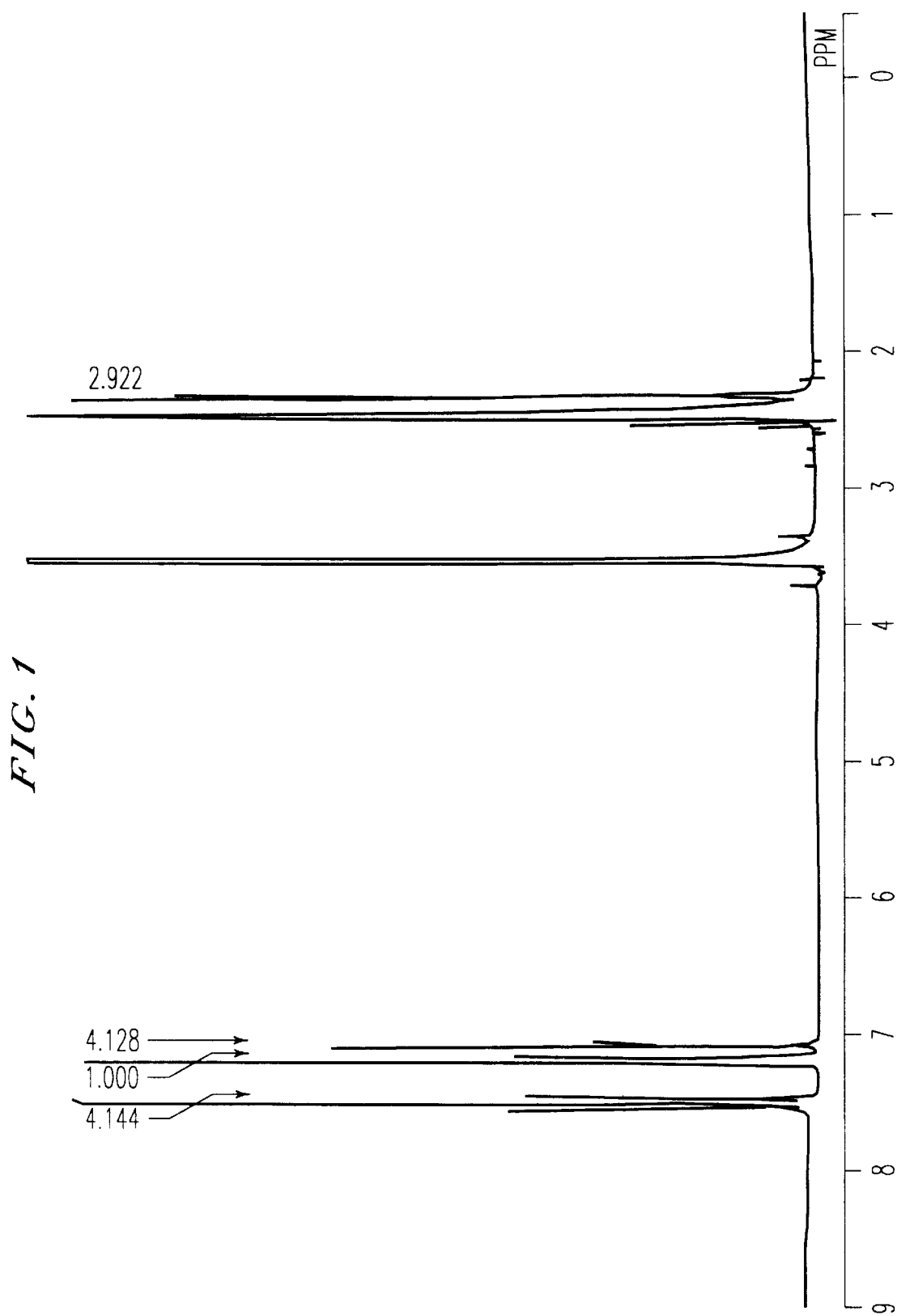
FIG. 1, FIG. 2, FIG. 3, and FIG. 4 show $^1$H-NMR spectrum charts of the compounds obtained in Preparation Example 4, Preparation Example 5, Preparation Example 6, and Preparation Example 7, respectively.

One of the arylenediamine derivatives used in the organic device of the present invention is a compound having 6 or more benzene ring skeletons which is represented by the general formula (I):

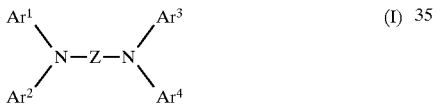

In the general formula (I) described above, Z represents a phenylene group, and $Ar^1$, $Ar^2$, $Ar^3$, and $Ar^4$ represent each an aryl group having 6 to 20 carbon atoms. Specific examples of the aryl group include phenyl group, naphthyl group, biphenyl group, anthranyl group, acenaphthyl group, phenanthryl group, pyrenyl group, and the like. The p-phenylene group represented by Z and the aryl group represented by each of $Ar^1$ to $Ar^4$ may each be substituted with alkyl groups having 1 to 6 carbon atoms, such as methyl group, ethyl group, n-propyl group, isopropyl group, cyclopropyl group, n-butyl group, isobutyl group, sec-butyl group, tert-butyl group, cyclobutyl group, n-pentyl group, cyclopentyl group, n-hexyl group, cyclohexyl group, and the like; alkoxy groups having 1 to 6 carbon atoms, such as methoxy group, ethoxy group, n-propoxy group, isopropoxy group, cyclopropoxy group, n-butoxy group, isobutoxy group, sec-butoxy group, tert-butoxy group, cyclobutoxy group, n-pentoxy group, cyclopentoxy group, n-hexoxy group, cyclohexoxy group, and the like; or phenyl groups.

$Ar^1$, $Ar^2$, $Ar^3$, and $Ar^4$ described above may be the same with each other or different from each other, and the combination of $Ar^1$, $Ar^2$, $Ar^3$, $Ar^4$, and Z of the central skeleton must have 6 or more benzene ring skeletons.

The present inventors have undertaken further studies particularly on the hole transporting layer with the object of improving durability of organic EL devices.

As the result of the studies, it has been discovered that the life of light emission of an organic EL device can be remarkably increased when, among the p-phenylenediamine derivatives represented by the general formula (I), a p-phenylenediamine derivative having 4 biphenyl groups which is represented by the general formula (II) is used for the hole transporting layer:

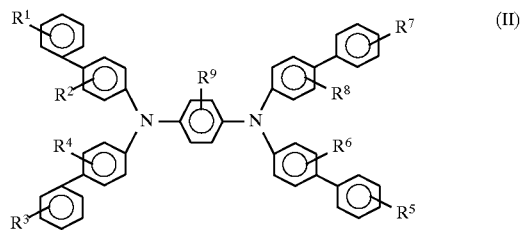

It has also been discovered that the arylenediamine derivatives used in the organic EL device of the present invention also include 4,4'-biphenylenediamine derivative having 5 biphenyl groups which is represented by the general formula (III):

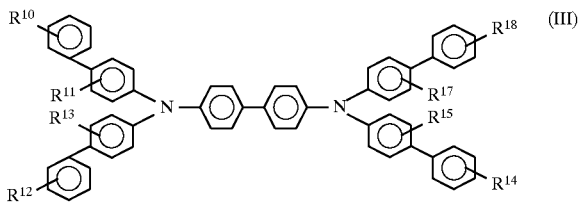

and that durability of an organic EL device can be remarkably increased when the 4,4'-biphenylenediamine derivative is used for a hole transporting layer. The diamine derivatives represented by the general formulae (II) and (III) are novel compounds which are not described in literature.

In the general formulae (II) and (III), $R^1$ to $R^{17}$ represent each a hydrogen atom; an alkyl group having 1 to 6 carbon atoms, such as methyl group, ethyl group, n-propyl group, isopropyl group, cyclopropyl group, n-butyl group, isobutyl group, sec-butyl group, tert-butyl group, cyclobutyl group, n-pentyl group, cyclopentyl group, n-hexyl group, cyclohexyl group, or the like; an alkoxy group having 1 to 6 carbon atoms, such as methoxy group, ethoxy group, n-propoxy group, isopropoxy group, cyclopropoxy group, n-butoxy group, isobutoxy group, sec-butoxy group, tert-butoxy group, cyclobutoxy group, n-pentoxy group, cyclopentoxy group, n-hexoxy group, cyclohexoxy group, or the like; or a phenyl group.

In the general formula (II), $R^1$ to $R^9$ may be the same with each other or different from each other. $R^1$ and $R^2$, $R^2$ and $R^4$, $R^3$ and $R^4$, $R^5$ and $R^6$, $R^6$ and $R^8$, $R^7$ and $R^8$, $R^2$ and $R^9$, $R^4$ and $R^9$, $R^6$ and $R^9$, and $R^8$ and $R^9$, may each form a ring by being bonded to each other.

In general formula (III), $R^{10}$ to $R^{17}$ may be the same with each other or different from each other; and $R^{10}$ and $R^{11}$, $R^{11}$ and $R^{13}$, $R^{12}$ and $R^{13}$, $R^{14}$ and $R^{15}$, $R^{15}$ and $R^{17}$, and $R^{16}$ and $R^{17}$, may each form a ring by being bonded to each other.

The life of light emission of an organic EL device can be remarkably increased by using the p-phenylenediamine derivative represented by the general formula (II) described above or the 4,4'-biphenylenediamine derivative represented by the general formula (III) described above as a component, particularly as a material of a hole transporting layer, of the organic EL device.

Processes for producing the p-phenylenediamine derivative represented by the general formula (II) described above and the 4,4'-biphenylenediamine derivative represented by the general formula (III) described above are described in the following.

The p-phenylenediamine derivative represented by the general formula (II) can be produced, for example, by the following processes:

(i) A process comprising condensing a p-phenylenediamine represented by the general formula (IV):

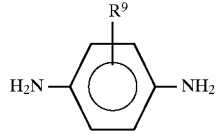

[wherein $R^9$ is the same as that described above] and a halogenated aryl compound represented by the general formula (V):

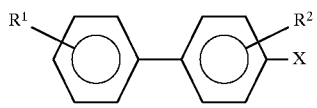

[wherein X represents a halogen atom (fluorine, chlorine, bromine, or iodine), and $R^1$ and $R^2$ are the same as those described above];

(ii) A process comprising condensing a protected diamine derivative represented by the general formula (VI):

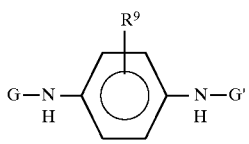

[wherein G and G' represent each a protective group, such as acetyl group, benzyl group, trifluoroacetyl group, t-butoxycarboxyl group, or the like, preferably acetyl group, and may be the same or different, and $R^9$ is the same as that described above], removing the protective groups G and G' in the condensation product, and subsequently condensing the products similarly;

(iii) A process comprising condensing an amine represented by the general formula (VII):

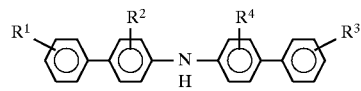

[wherein $R^1$ to $R^4$ are the same as those described above] and a dihalogenated aryl compound represented by the general formula (VIII):

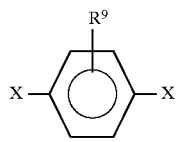

[wherein X and $R^9$ are the same as those described above, and two X may be the same with each other or different from each other]; and (iv) A process comprising condensing the amine represented by the general formula (VII) described above, a halogenated aminoaryl compound represented by the general formula (IX):

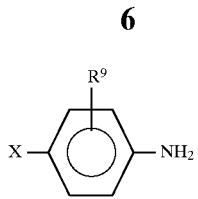

[wherein X and $R^9$ are the same as those described above] and the halogenated aryl compound represented by the general formula (V) described above.

Specific examples of the p-phenylenediamine represented by the general formula (IV) include:

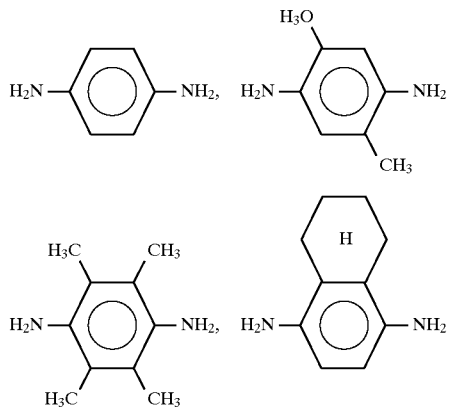

Specific examples of the halogenated aryl compound represented by the general formula (V) include:

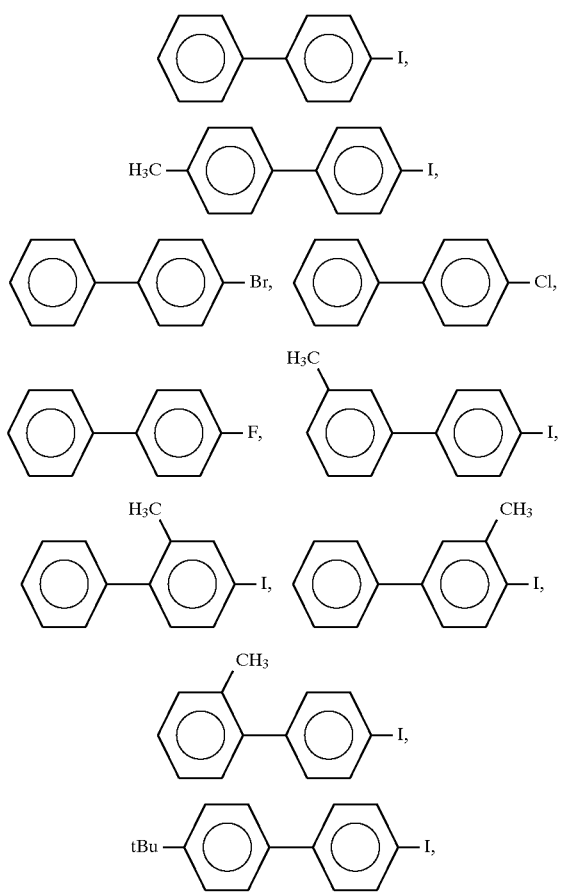

-continued

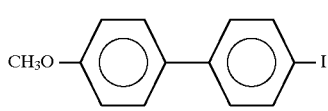

(tBu: t-butyl group; the same in the following formulae)
Specific examples of the protected diamine derivative represented by the general formula (VI) include:

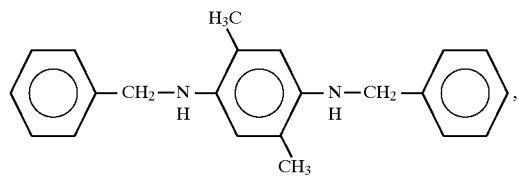

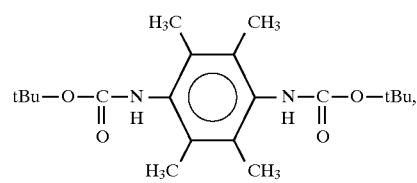

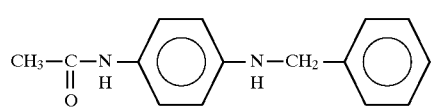

Specific examples of the amine represented by the general formula (VII) include:

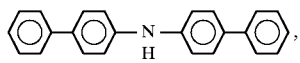

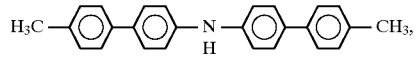

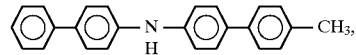

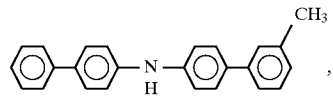

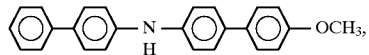

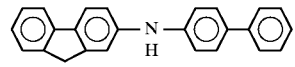

Specific examples of the dihalogenated aryl compound represented by the general formula (VIII) include:

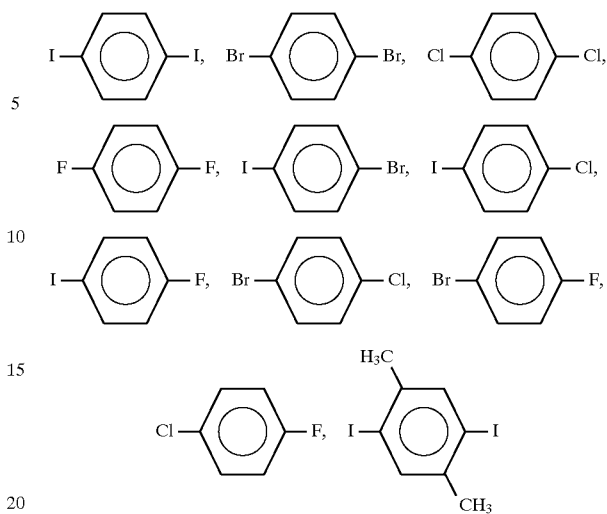

Specific examples of the halogenated aminoaryl compound represented by the general formula (IX) include:

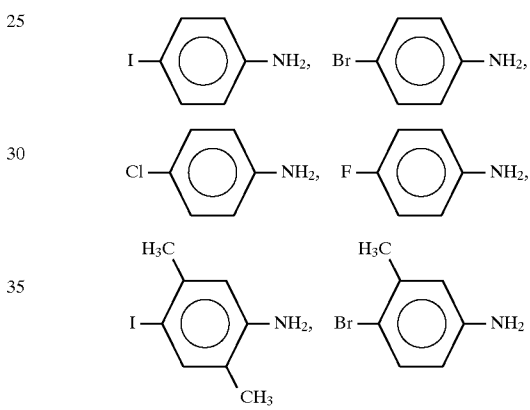

In the process (ii), it is possible that an asymmetric diamine derivative is produced by stepwise removal of the protective groups G and G'.

In the condensation reactions (i) to (iv) described above, a base is used. As the base, for example, a carbonate, a hydroxide, or a hydride of an alkali metal or an alkaline earth metal, an amine, an alkyllithium, or the like, is used. Potassium carbonate is particularly preferable as the base. In the condensation reactions, a catalyst can be used if necessary. Examples of the catalyst include copper, salts of copper, nickel, palladium, and the like. As the shape of the catalyst, powder form is preferable. The particle size is preferably in the range of 10 nm to 1 mm, more preferably in the range of 100 to 500 nm. The condensation reactions may be conducted in a solid phase without using a solvent or in a solvent. It is more advantageous that the condensation reactions are conducted in a solvent. In this case, a solvent having a higher boiling point is preferable. For example, nitrobenzene, dimethylsulfoxide, dimethylformamide, sulfolane, or the like can be used. Among these solvents, dimethylsulfoxide is particularly preferable.

The temperature of the condensation reactions is selected generally in the range of 100° to 400° C., preferably in the range of 150° to 250° C. The pressure of the condensation reactions is generally an atmospheric pressure. However, the reactions may be conducted under an elevated pressure if necessary. The time of the condensation reactions is varied depending on the types of the materials used, the type of the catalyst, and the temperature. The time is generally about 3 to 36 hours.

The 4,4'-biphenylenediamine derivative represented by the general formula (III) can be produced, for example, by the following processes:

(i) A process comprising condensing a protected diamine derivative represented by the general formula (X):

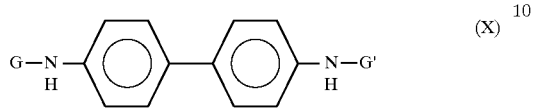

(X)

[wherein G and G' are the same as those described above] and a halogenated aryl compound represented by the general formula (XI):

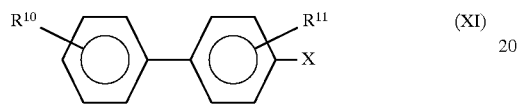

(XI)

[wherein X, $R^{10}$, and $R^{11}$ are the same as those described above], removing the protective groups in the condensation product, and subsequently condensing the products similarly;

(ii) A process comprising condensing an amine represented by the general formula (XII):

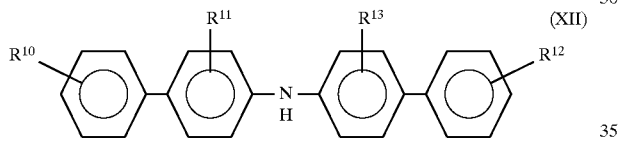

(XII)

[wherein $R^{10}$ to $R^{13}$ are the same as those described above] and a dihalogenated aryl compound represented by the general formula (XIII):

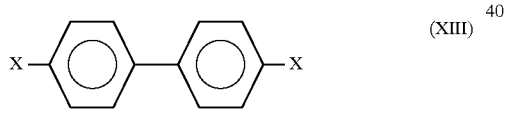

(XIII)

[wherein X is the same as that described above, and two X may be the same with each other or different from each other]; and (iii) A process comprising condensing an amine represented by the general formula (XII) described above and a halogenated aminoaryl compound represented by the general formula (XIV):

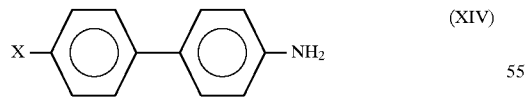

(XIV)

[wherein X is the same as that described above, and the amino group may be protected with a protective group].

Specific examples of the protected diamine derivative represented by the general formula (X) described above include:

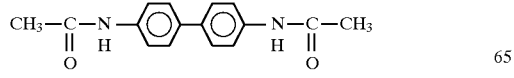

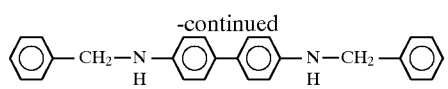

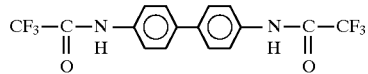

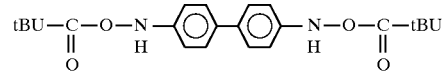

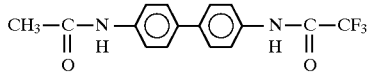

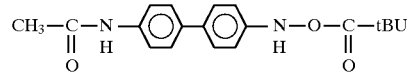

Specific examples of the halogenated aryl compound represented by the general formula (XI) include:

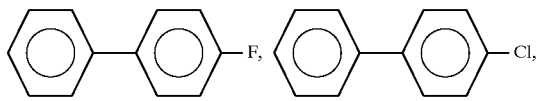

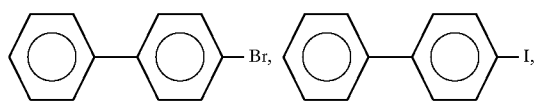

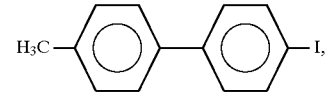

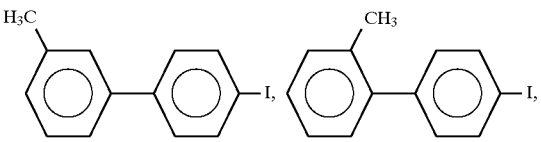

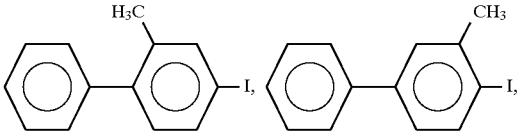

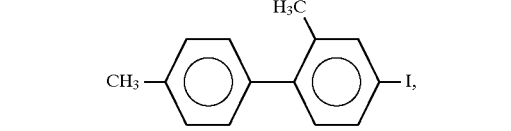

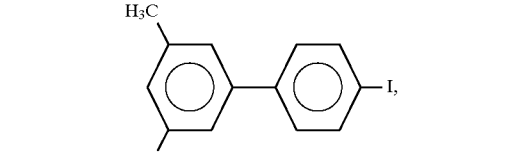

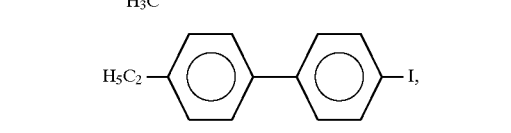

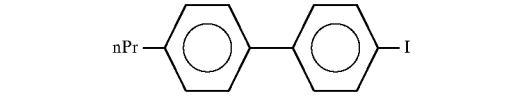

(nPr: n-propyl group; the same in the following formulae),

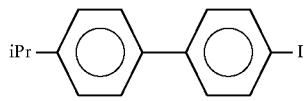

(iPr: isopropyl group; the same in the following formulae),

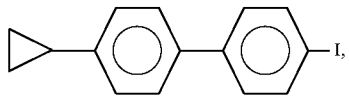

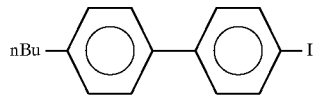

(nBu: n-butyl group; the same in the following formulae),

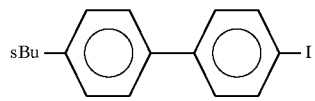

(sBu: sec-butyl group; the same in the following formulae),

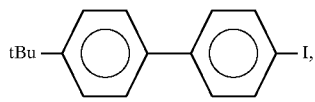

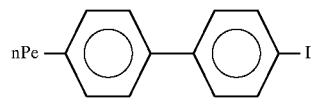

(nPe: n-pentyl group; the same in the following formulae)

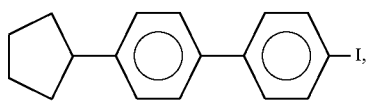

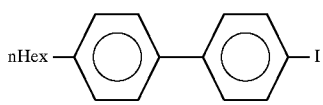

(nHex: n-hexyl group; the same in the following formulae)

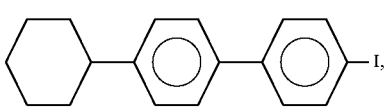

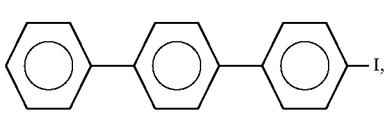

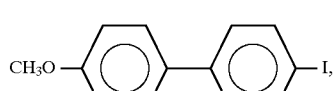

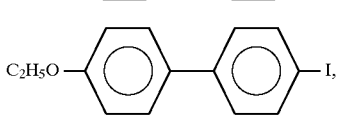

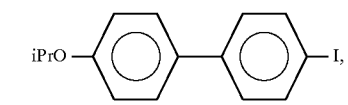

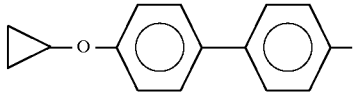

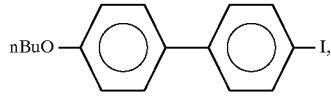

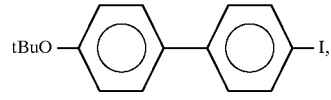

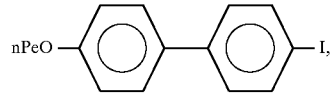

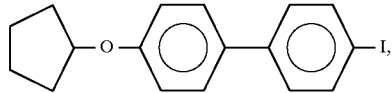

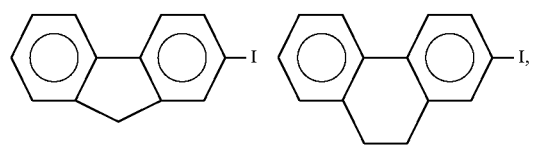

Specific examples of the amine represented by the general formula (XII) include:

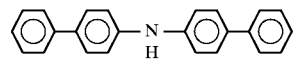

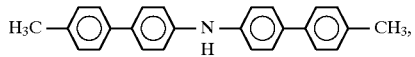

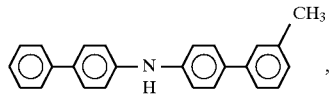

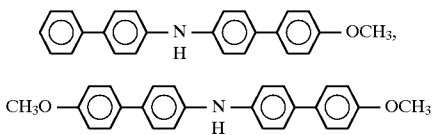

Specific examples of the dihalogenated aryl compound represented by the general formula (XIII) include:

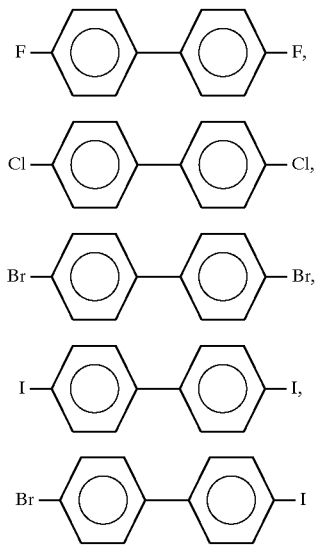

Specific examples of the halogenated aminoaryl compound represented by the general formula (XIV) include:

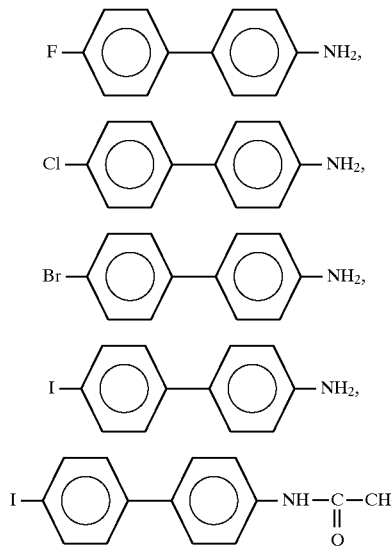

In the process (i), it is possible that an asymmetric diamine derivative is produced by stepwise removal of the protective groups G and G'.

In the process (iii), it is possible that an asymmetric diamine derivative is produced by a process including protecting the amino groups in the halogenated aminoaryl compound represented by the general formula (XIV) by protective groups, and subsequently removing the protective groups in separate steps. Examples of the protective group include the same groups described above in the examples of G and G'.

The conditions in the condensation reactions (i) to (iii) are the same as those in the processes for producing the p-phenylenediamine derivative represented by the general formula (II) described above.

Specific examples of the p-phenylenediamine derivative represented by the general formula (I) described above include the following compounds:

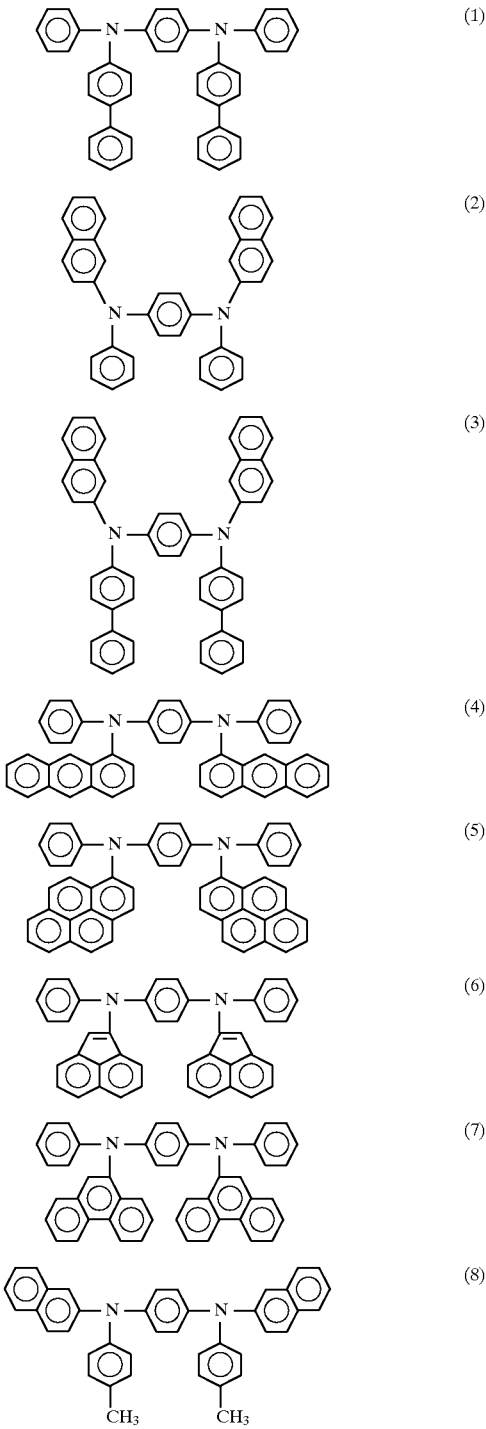

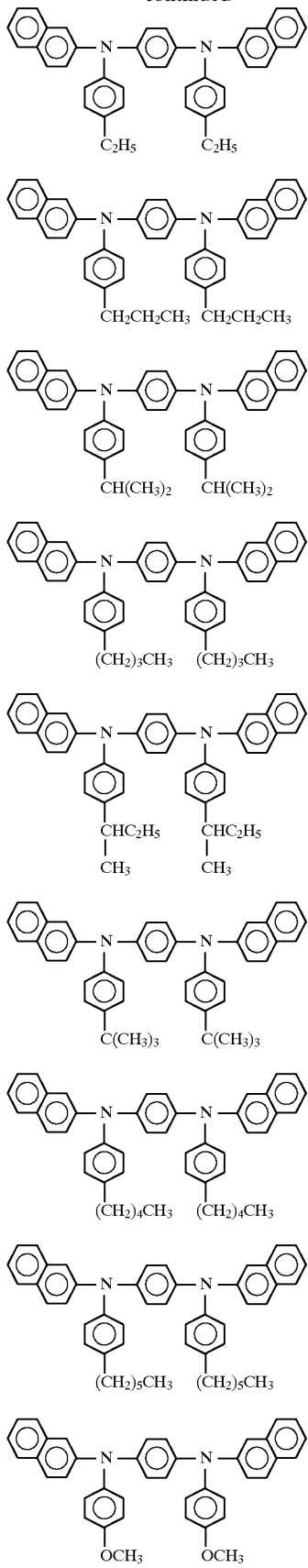
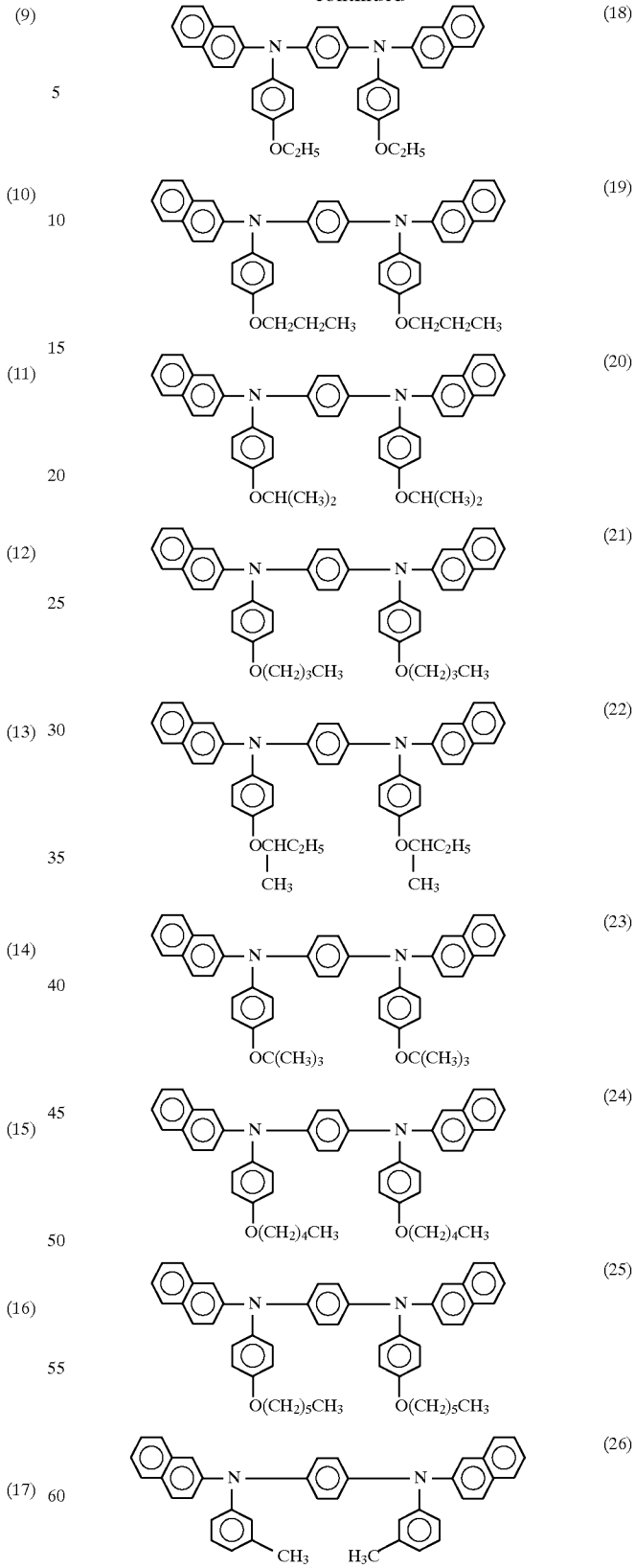
Among these compounds, compounds represented by the general formula (I) in which $Ar^1$, $Ar^2$, $Ar^3$, and $Ar^4$ are each naphthyl group or biphenyl group are preferable.

Specific examples of the p-phenylenediamine derivative represented by the general formula (II) described above include the following compounds:
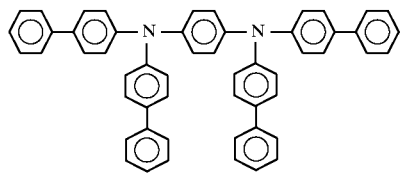 (27)
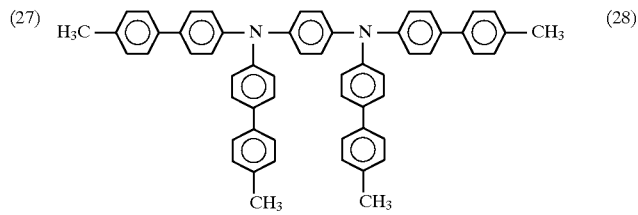 (28)
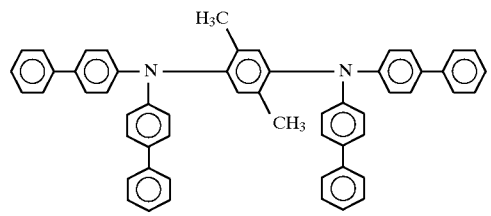 (29)
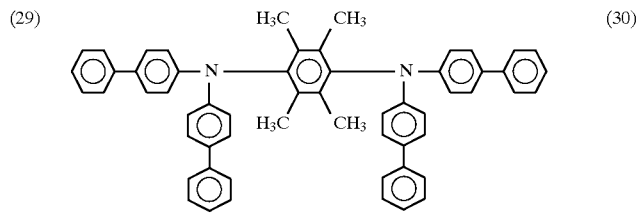 (30)
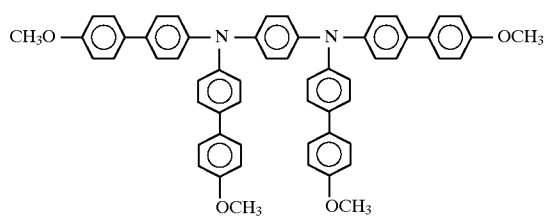 (31)
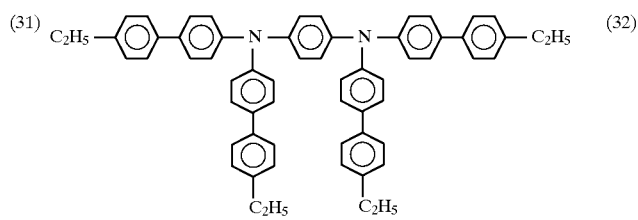 (32)
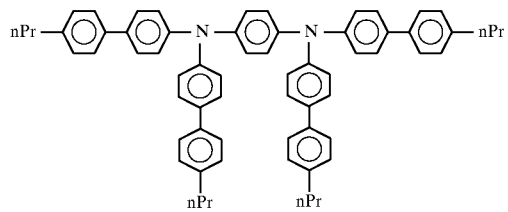 (33)
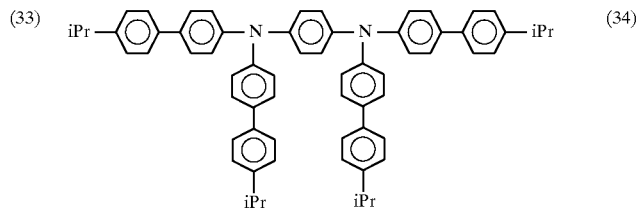 (34)
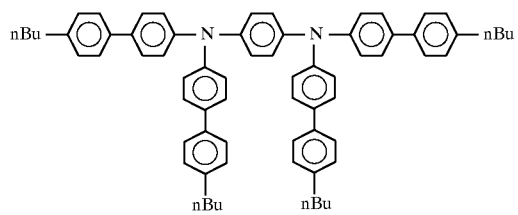 (35)
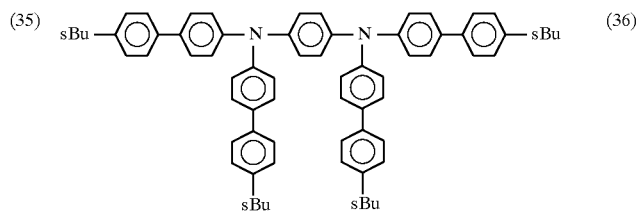 (36)
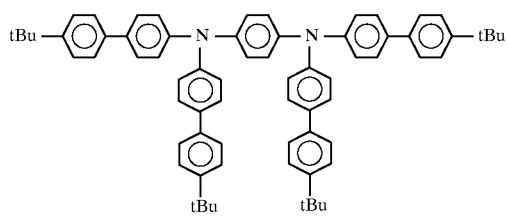 (37)
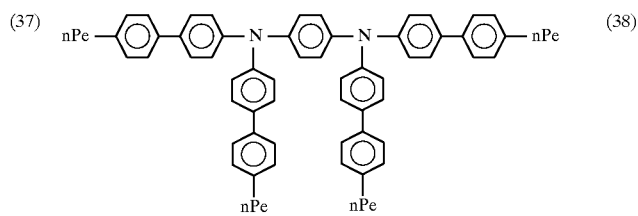 (38)
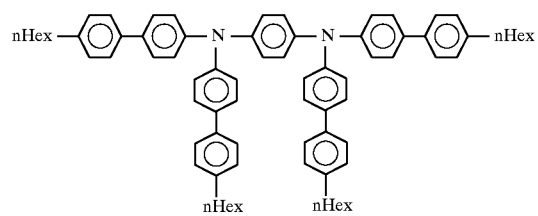 (39)

-continued
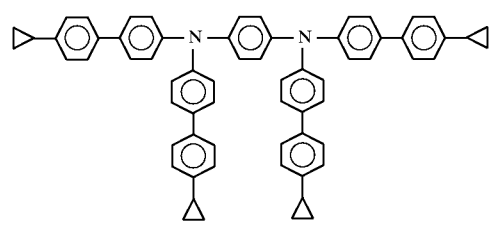
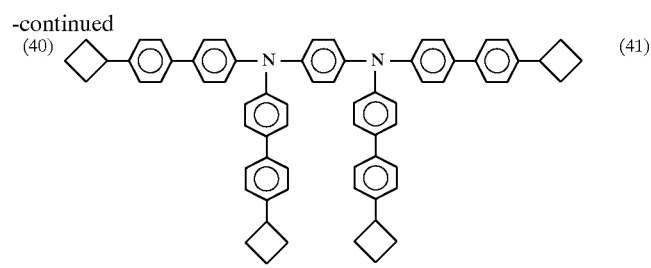
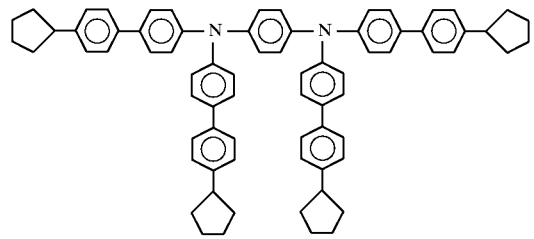
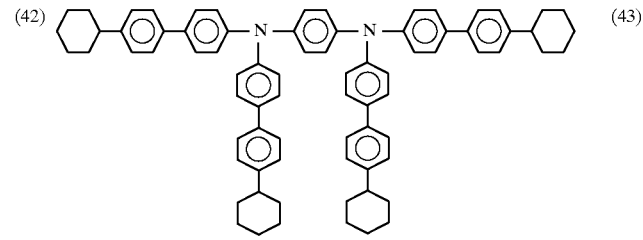
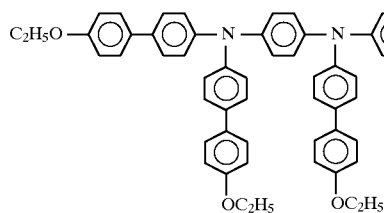
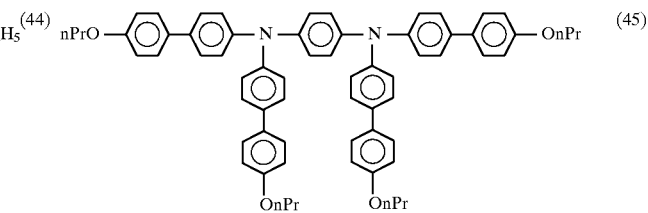
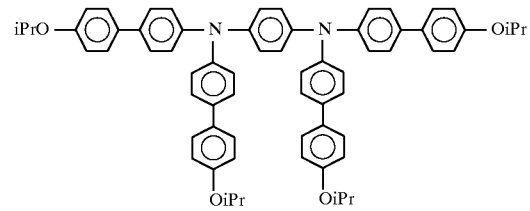
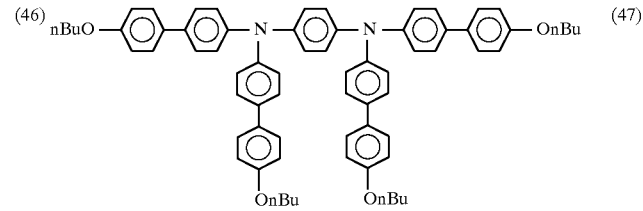
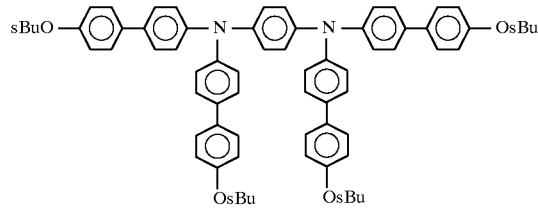
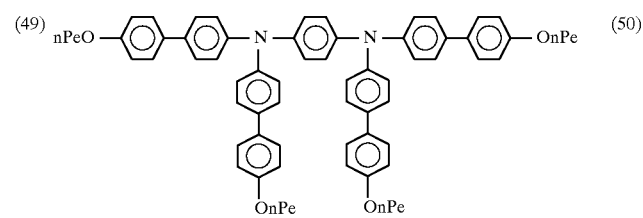
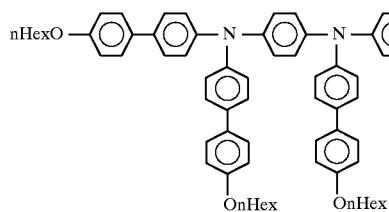
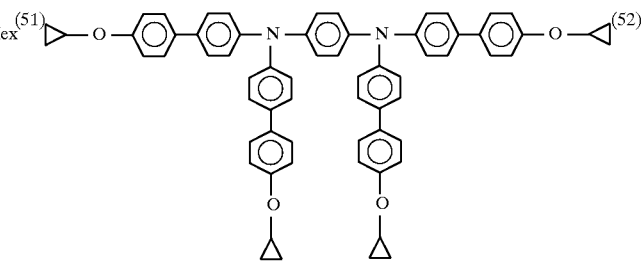

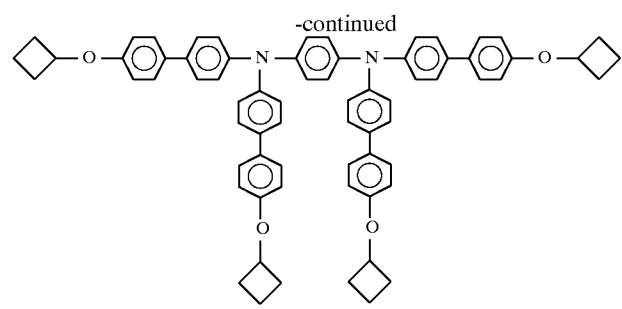
(53)
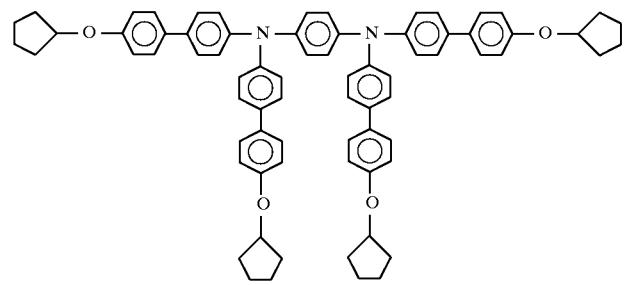
(54)
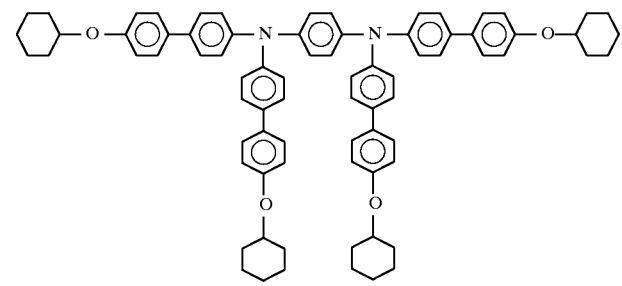
(55)
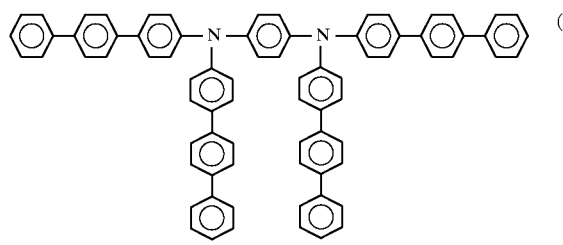
(56)
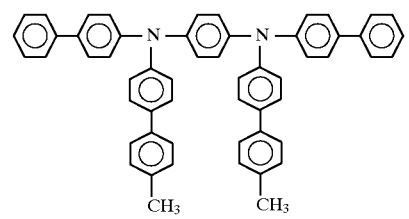
(57)
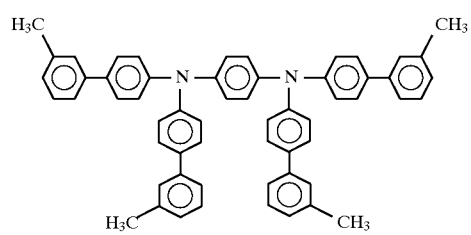
(58)
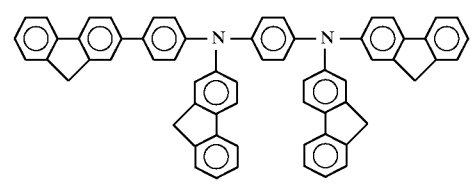
(59)
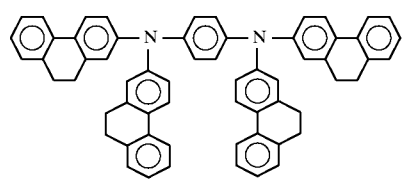
(60)

Specific examples of the 4,4'-biphenylenediamine derivative represented by the general formula (III) include the following compounds:
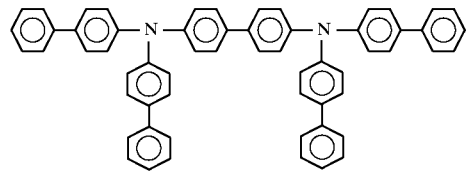 (61)
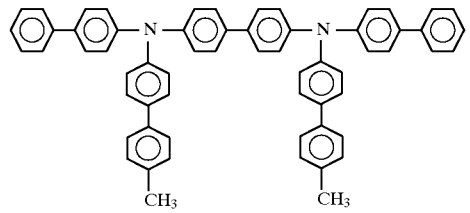 (62)
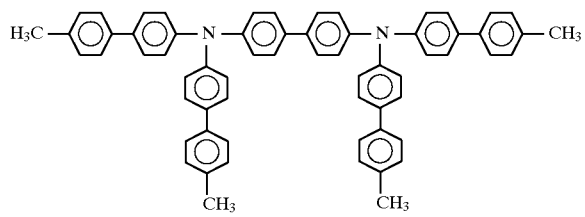 (63)
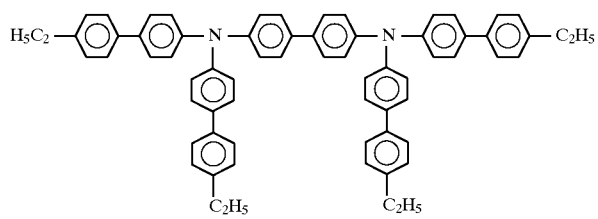 (64)
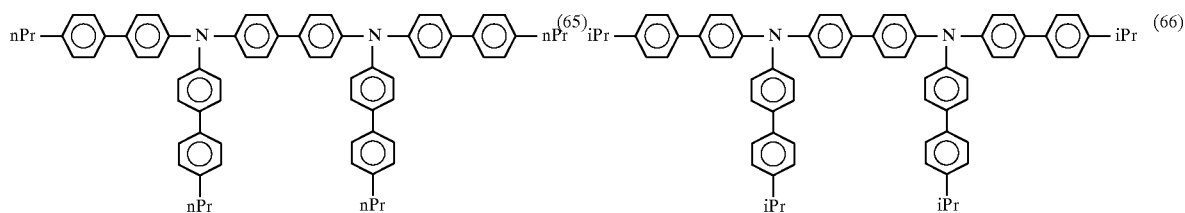 (65) (66)
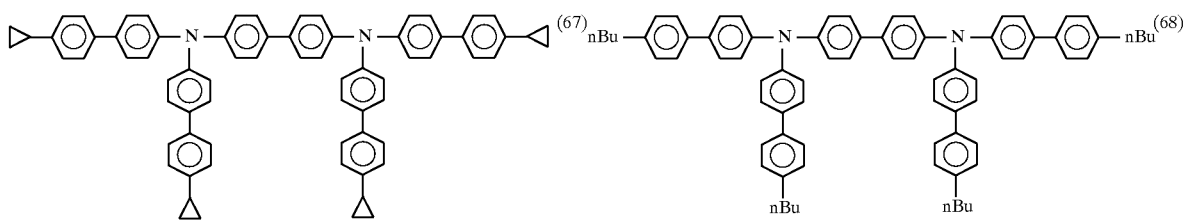 (67) (68)
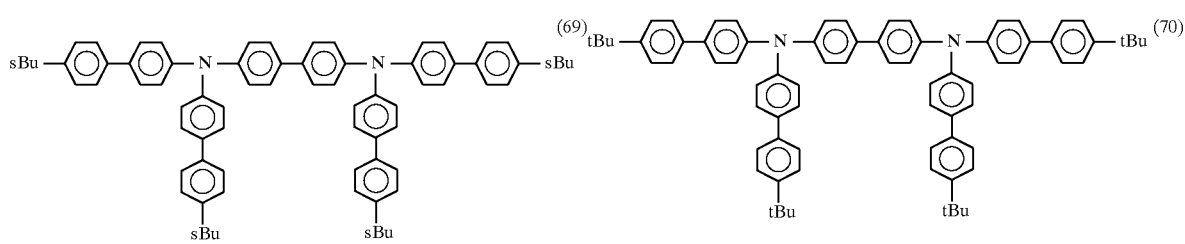 (69) (70)
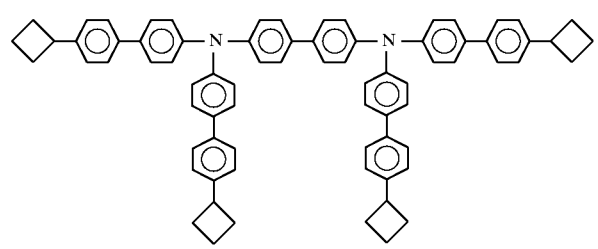 (71)

-continued
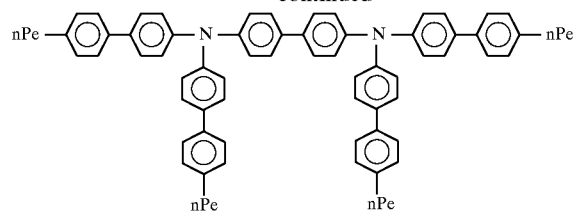 (72)
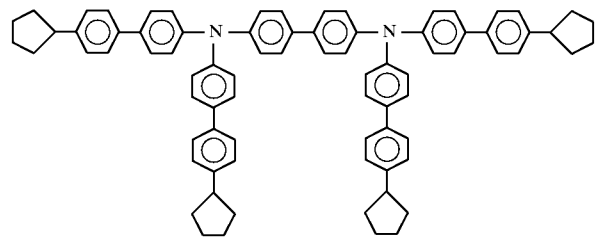 (73)
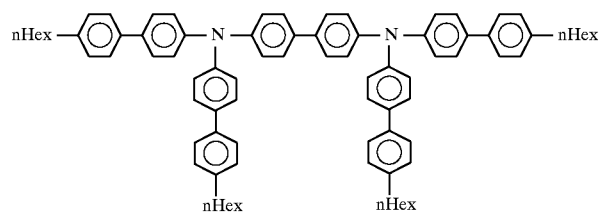 (74)
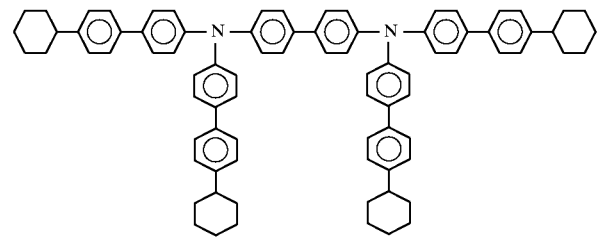 (75)
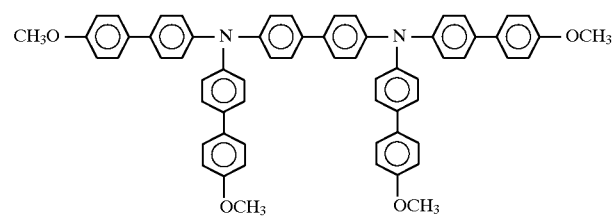 (76)
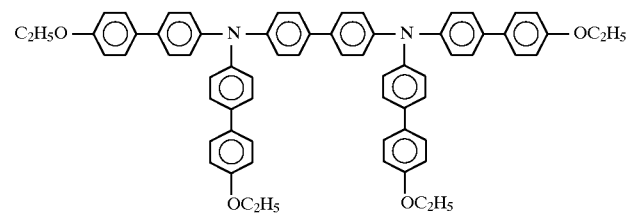 (77)
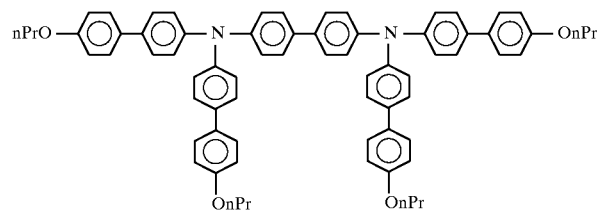 (78)

-continued
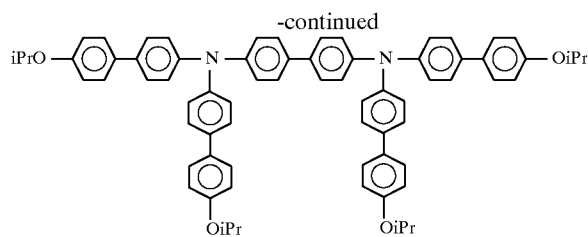
(79)
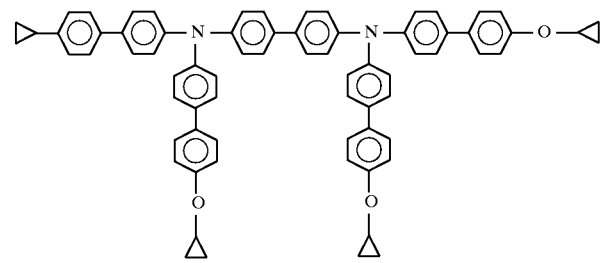
(80)
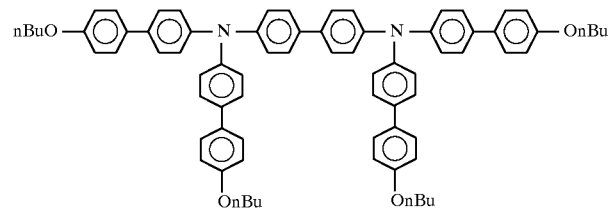
(81)
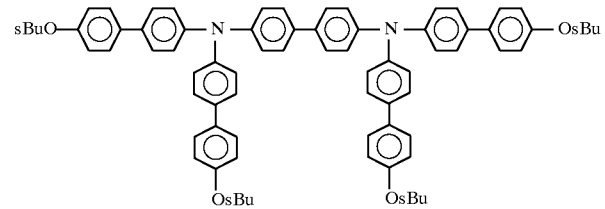
(82)
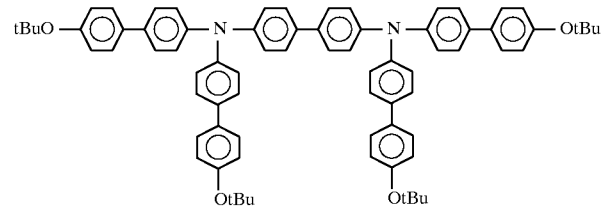
(83)
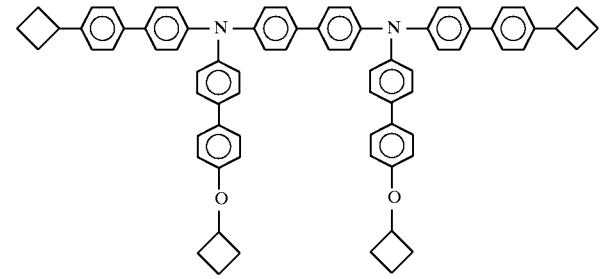
(84)
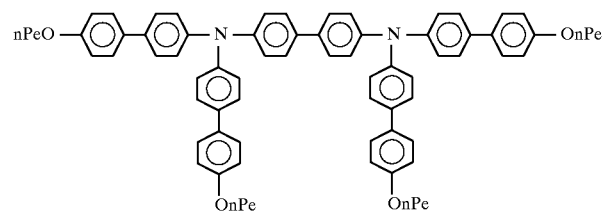
(85)

-continued
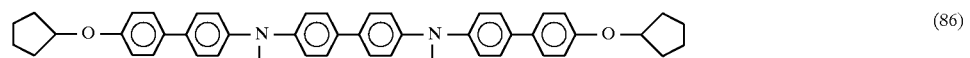  (86)
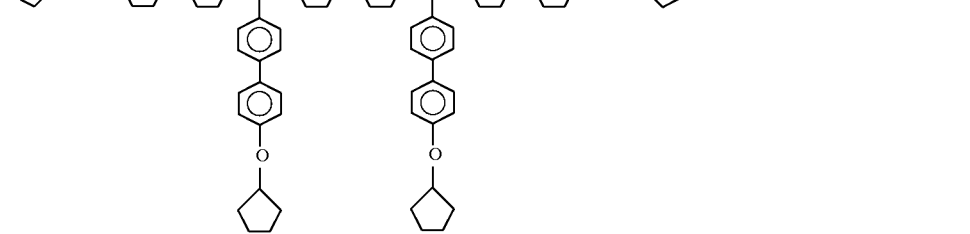  (87)
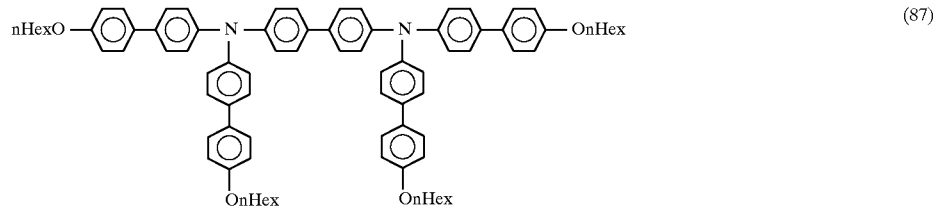  (88)
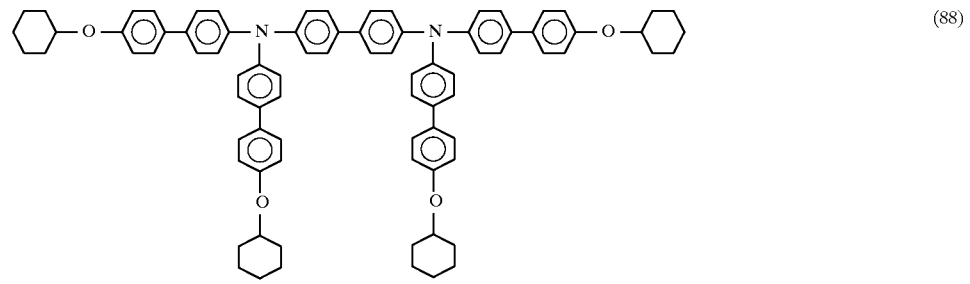  (89)
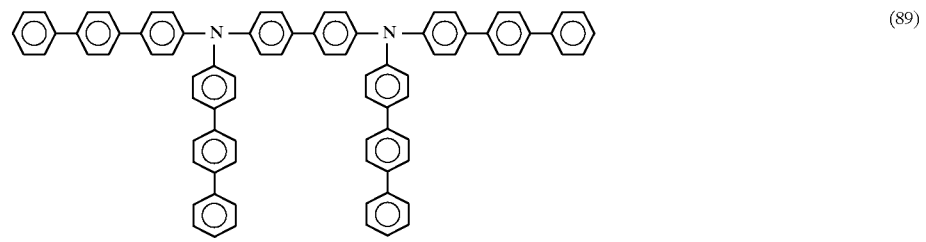
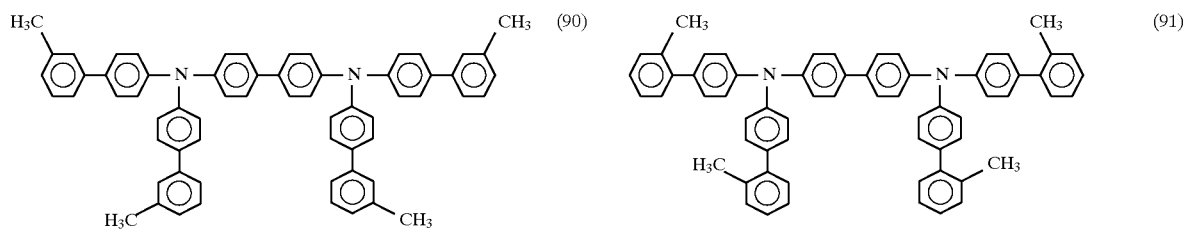  (90)  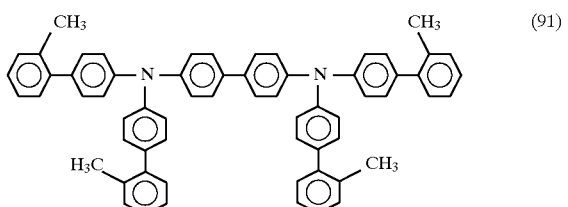  (91)
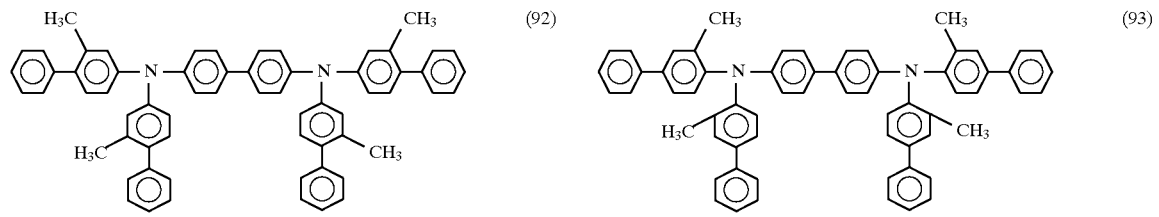  (92)  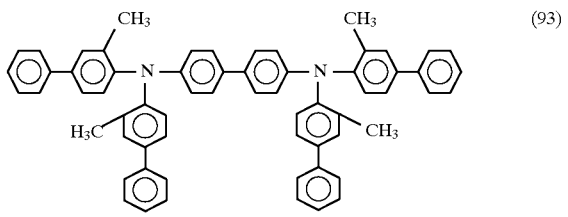  (93)

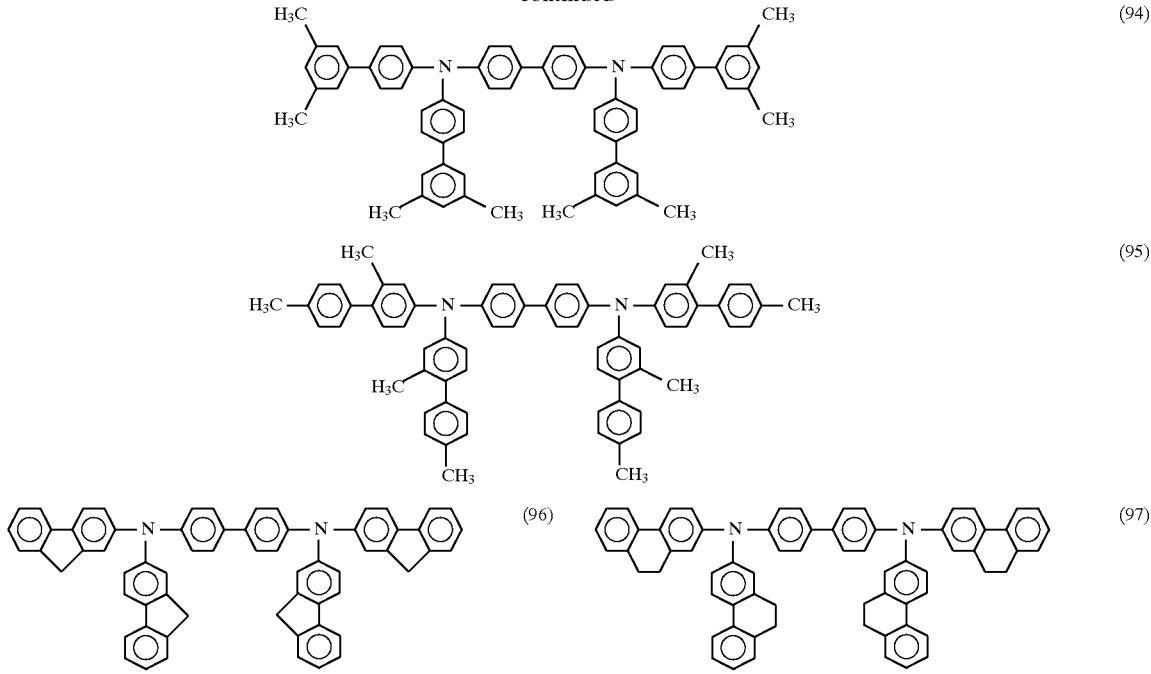

The organic EL device of the present invention at least contains the p-phenylenediamine derivative represented by the general formula (I) described above [including the compound represented by the general formula (II) described above] or the 4,4'-biphenylenediamine derivative represented by the general formula (III) described above. The diamine derivative may be contained in the organic EL device as a single type or as a combination of two or more types of the diamine derivative.

The construction of the organic EL device is, for example, (i) an anode/an organic light emitting layer/a cathode, (ii) an anode/a hole transporting layer/an organic light emitting layer/a cathode, (iii) an anode/an organic light emitting layer/an electron injecting layer/a cathode, or (iv) an anode/a hole transporting layer/an organic light emitting layer/an electron injecting layer/a cathode. The organic EL device of the present invention may have any of the constructions (i) to (iv) as long as at least one of the layers of compounds placed between a pair of electrodes (an anode and a cathode) [the organic light emitting layer in the device having the construction (i) described above, the hole transporting layer or the organic light emitting layer in the device having the construction (ii), the organic light emitting layer and the electron injecting layer in the device having the construction (iii), and the hole transporting layer, the organic light emitting layer, and the electron injecting layer in the device having the construction (iv)] contains the p-phenylenediamine derivative represented by the general formula (I) described above [including the compound represented by the general formula (II) described above] or the 4,4'-biphenylenediamine derivative represented by the general formula (III). It is preferred that the organic EL device having any of these constructions is supported on a substrate. The substrate is not particularly limited, and a substrate which is conventionally used in organic EL devices, such as glass, a transparent plastics, quartz, or the like, may be used.

The layer containing the p-phenylenediamine derivative or the 4,4'-biphenylenediamine derivative which is the characteristic part of the organic EL device of the present invention is preferably a hole transporting layer or an organic light emitting layer, more preferably a hole transporting layer.

The hole transporting layer containing the p-phenylenediamine derivative or the 4,4'-biphenylenediamine derivative may have a single layer structure consisting of a layer of the p-phenylenediamine derivative or the 4,4'-biphenylenediamine derivative, or a multi-layer structure comprising a layer of the p-phenylenediamine derivative or the 4,4'-biphenylenediamine derivative and a layer of a substance which has conventionally been used as a material of a hole transporting layer of an organic EL device. The hole transporting layer may also have a single layer structure consisting of, or a multi-layer structure comprising, a layer of a mixture of the p-phenylenediamine derivative or the 4,4'-biphenylenediamine derivative and a substance which has conventionally been used as a material of a hole transporting layer of an organic EL device.

The hole transporting layer containing the p-phenylenediamine derivative or the 4,4'-biphenylenediamine derivative can be formed by using the p-phenylenediamine derivative or the 4,4'-biphenylenediamine derivative and other materials for the hole transporting layer, if necessary, by the vacuum vapor deposition method, the casting method, the coating method, the spin coating method, or the like. The hole transporting layer may also be formed on a transparent polymer, such as a polycarbonate, a polyurethane, polystyrene, a polyarylate, a polyester, or the like, by the casting method, the coating method, or the spin coating method, using a solution in which the p-phenylenediamine derivative or the 4,4'-biphenylenediamine derivative is dispersed, or by the simultaneous vapor deposition of the p-phenylenediamine derivative or the 4,4'-biphenylenediamine derivative with the transparent polymer.

The organic light emitting layer containing the p-phenylenediamine derivative or the 4,4'- biphenylenediamine derivative may have a single layer structure consisting of a layer of the p-phenylenediamine derivative or the 4,4'-biphenylenediamine derivative, or a multi-layer structure comprising a layer of the p-phenylenediamine derivative or the 4,4'-biphenylenediamine derivative and a layer of a substance which has conventionally been used as a material of an organic light emitting layer of an organic EL device. The organic light emitting layer may also have a single layer structure consisting of, or a multi-layer structure comprising, a layer of a mixture of the p-phenylenediamine derivative or the 4,4'-biphenylenediamine derivative and a substance which has conventionally been used as a material of an organic light emitting layer of an organic EL device. The organic light emitting layer containing the p-phenylenediamine derivative or the 4,4'-biphenylenediamine derivative can be formed by using the p-phenylenediamine derivative or the 4,4'-biphenylenediamine derivative and other materials for the organic light emitting layer, if necessary, by the vacuum vapor deposition method, the casting method, the coating method, the spin coating method, or the like.

In the organic EL device of the present invention, layers other than the layer containing the p-phenylenediamine derivative or the 4,4'-biphenylenediamine derivative may be formed by using materials which are used in conventional organic EL devices.

For example, as the material of the anode, a metal, an alloy, an electric conductive compound, or a mixture of these compounds, which has a great work function (4 eV or more), is preferably used. Specific examples of the material of the anode include metals, such as Au and the like; and dielectric transparent materials, such as CuI, ITO, $SnO_2$, ZnO, and the like. The anode can be prepared by forming a thin layer of the material described above by a method, such as the vapor deposition method, the sputtering method, or the like. When the light emitted from the organic light emitting layer is obtained through the anode, it is preferred that the transmittance of the anode is greater than 10%. It is also preferred that the electric resistance of the sheet as the anode is several hundred $\Omega/\square$ or less. The thickness of the anode is selected generally in the range of 10 nm to 1 $\mu$m, preferably in the range of 10 to 200 nm, though the thickness depends on the material used.

On the other hand, as the material of the cathode, a metal, an alloy, an electric conductive compound, or a mixture of these compounds, which has a small work function (4 eV or less), is preferably used. Specific examples of the material of the cathode include sodium, lithium, a magnesium/copper mixture, $Al/Al_2O_3$, indium, and the like. The cathode can be prepared by forming a thin layer of the material described above by a method, such as the vapor deposition method, the sputtering method, or the like. When the light emitted from the organic light emitting layer is obtained through the cathode, it is preferred that the transmittance of the cathode is greater than 10%. It is also preferred that the electric resistance of the sheet as the cathode is several hundred $\Omega/\square$ or less. The thickness of the anode is selected generally in the range of 10 nm to 1 $\mu$m, preferably in the range of 50 to 200 nm, though the thickness depends on the material used.

In view of efficiently obtaining the light emitted from the organic light emitting layer, it is preferred that at least one of the anode and the cathode is formed with a transparent or semi-transparent material.

When the organic light emitting layer in the organic EL device of the present invention is formed with the p-phenylenediamine derivative or the 4,4'-biphenylenediamine derivative and other substances, as the other substance used in addition to the p-phenylenediamine derivative or the 4,4'-biphenylenediamine derivative, for example, a compound which has the property suitable for forming a thin layer, such as a multi-ring condensed aromatic compound, a fluorescent bleaching agent like a benzoxazole bleaching agent, a benzothiazole bleaching agent, a benzimidazole bleaching agent, or the like, a metal chelated oxanoid compound, a distyrylbenzene compound, or the like, can be used.

Specific examples of the multi-ring condensed aromatic compound described above include condensed ring light emitting compounds having a skeleton of anthracene, naphthalene, phenanthrene, pyrene, chrysene, perylene, or the like, and other condensed ring light emitting substances having 8 to 20, preferably 8 condensed rings.

Examples of the fluorescent bleaching agent described above, such as a benzoxazole bleaching agent, a benzothiazole bleaching agent, a benzimidazole bleaching agent, or the like, include compounds disclosed in Japanese Patent Application Laid-Open No. Showa 59(1984)-194393. Typical examples of the fluorescent bleaching agent include benzoxazole bleaching agents, such as 2,5-bis(5,7-di-t-pentyl-2-benzoxazolyl)-1,3,4-thiadiazole, 4,4'-bis(5,7-t-pentyl-2-benzoxazolyl)stilbene, 4,4'-bis(5,7-di(2-methyl-2-butyl)-2-benzoxazolyl)stilbene, 2,5-bis(5,7-di-t-pentyl-2-benzoxazolyl)thiophene, 2,5-bis(5-($\alpha,\alpha$-dimethylbenzyl)-2-benzoxazolyl)thiophene, 2,5-bis(5,7-di-(2-methyl-2-butyl)-2-benzoxazolyl)3,4-diphenyl-thiophene, 2,5-bis(5-methyl-2-benzoxazolyl)thiophene, 4,4'-bis(2-benzoxazolyl)biphenyl, 5-methyl-2-(2-(4-(5-methyl-2-benzoxazolyl)phenyl)vinyl)benzoxazol, 2-(2-(4-chlorophenyl)vinyl)naphtho(1,2-d)oxazol, and the like; benzothiazole bleaching agents, such as 2,2'-(p-phenylenedivinylene)-bisbenzothiazole, and the like; and benzimidazole bleaching agents, such as 2-(2-(4-carboxylphenyl)vinyl)benzimidazole, and the like.

As the metal chelated oxanoid compound described above, for example, compounds disclosed in Japanese Patent Application Laid-Open No. Showa 63(1991)-295695 can be used. Typical examples of the metal chelated oxanoid compound include metal complexes of 8-hydroxyquinoline derivatives, such as tris(8-quinolinol)aluminum, bis(8-quinolinol)magnesium, bis[benzo(f)-8-quinolinol]zinc, bis(2-methyl-8-quinolinolato)aluminum oxide, tris(8-quinolinol)indium, tris(5-methyl-8-quinolinol)aluminum, 8-quinolinollithium, tris(5-chloro-8-quinolinol)gallium, bis(5-chloro-8-quinolinol)calcium, poly(zinc(II)-bis(8-hydroxy-5-quinolinonyl)methane); dilithium epindolidione; and the like.

As the distyrylbenzene compound described above, for example, compounds disclosed in European Patent No. 0373582 can be used. Specific examples of the distyrylbenzene compound include 1,4-bis(2-methylstyryl)benzene, 1,4-bis(3-methylstyryl)benzene, 1,4-bis(4-methylstyryl)benzene, distyrylbenzene, 1,4-bis(2-ethylstyryl)benzene, 1,4-bis(3-ethylstyryl)benzene, 1,4-bis(2-methylstyryl)-2-methylbenzene, 1,4-bis(2-methylstyryl)-2-ethylbenzene, and the like.

The distyrylpyrazine derivatives disclosed in Japanese Patent Application Laid-Open No. Heisei 2(1990)-252793 can also be used as the material of the organic light emitting layer. Typical examples of the distyrylpyrazine derivative include 2,5-bis(4-methylstyryl)pyrazine, 2,5bis(4-ethylstyryl)pyrazine, 2,5-bis[2-(1-naphthyl)vinyl]pyrazine, 2,5-bis(4-methoxystyryl)pyrazine, 2,5-bis[2-(4-biphenyl)vinyl]pyrazine, 2,5-bis[2-(1-pyrenyl)vinyl]pyrazine, and the like.

Dimethylidine derivatives disclosed in European Patent No. 0388768 and Japanese Patent Application Laid-Open No. Heisei 3(1991)231970 can also be used as the material of the organic light emitting layer. Typical examples of the dimethylidine derivative include 1,4-phenylenedimethylidine, 4,4'-biphenylenedimethylidine, 2,5-xylylenedimethylidine, 2,6-naphthylenedimethylidine, 1,4-biphenylenedimethylidine, 1,4-p-terephenylenedimethylidine, 9,10-anthracenediyldimethylidine, 4,4'-(2,2-di-t-butylphenylvinyl)biphenyl, 4,4'-(2,2-diphenylvinyl) biphenyl, like other compounds, and derivatives of these compounds.

Furthermore, coumarine derivatives disclosed in Japanese Patent Application Laid-Open No. Heisei 2(1990)-191694, perylene derivatives disclosed in Japanese Patent Application Laid-Open No. Heisei 2(1990)196885, naphthalene derivatives disclosed in Japanese Patent Application Laid-Open No. Heisei 2(1990)-255789, phthaloperynone derivatives disclosed in Japanese Patent Application Laid-Open No. Heisei 2(1990)-289676 and Japanese Patent Application Laid-Open No. Heisei 2(1990)-88689, and styrylamine derivatives disclosed in Japanese Patent Application Laid-Open No. Heisei 2(1990)-250292, can also be used as the material of the light emitting layer.

The material of the organic light emitting layer is selected from these compounds in accordance with the desired color of the emitted light and other desired properties. The organic light emitting layer of the organic EL device of the present invention may also be formed by additionally using a fluorescent substance as described in U.S. Pat. No. 4,769,292. The substance which is used as the base material in this case may be the p-phenylenediamine derivative, the 4,4'-biphenylenediamine derivative, or a material of the light emitting layer other than the p-phenylenediamine derivative and the 4,4'-biphenylenediamine derivative. The substance may also be a mixture of the p-phenylenediamine derivative or the 4,4'-biphenylenediamine derivative and a material of the organic light emitting layer. When the organic light emitting layer is formed by additionally using a fluorescent substance, it is preferred that the amount of the additionally used fluorescent substance is several percent by mol or less. The fluorescent substance emits light in response with the recombination of an electron and a hole, and carries a part of the light emitting function.

As the material of the organic light emitting layer, a compound which does not have the property of forming a thin layer may also be used. Specific examples of such a compound include 1,4-diphenyl-1,3-butadiene, 1,1,4,4-tetraphenyl-1,3-butadiene, tetraphenylcyclopentadiene, and the like. However, an organic EL device prepared by using the above-described material which does not have the property of forming a thin layer has a drawback in that the life of the device is short.

The hole transporting layer which is used, if necessary, in the organic EL device of the present invention may be a layer containing the p-phenylenediamine derivative or the 4,4'-biphenylenediamine derivative, or a layer containing none of the p-phenylenediamine derivative and the 4,4'-biphenylenediamine derivative as long as the organic light emitting layer contains the p-phenylenediamine derivative or the 4,4'-biphenylenediamine derivative. As the material of the hole transporting layer other than the p-phenylenediamine derivative or the 4,4'-biphenylenediamine derivative, various types of substance which have conventionally been used as a material of a hole transporting layer of an organic EL device can be used.

When a layer containing the p-phenylenediamine derivative or the 4,4'-biphenylenediamine derivative is formed as the hole transporting layer which is formed in the organic EL device of the present invention if necessary, the hole transporting layer may have, as described above, a single layer structure consisting of a layer of the p-phenylenediamine derivative or the 4,4'-biphenylenediamine derivative, a multi-layer structure comprising a layer of the p-phenylenediamine derivative or the 4,4'-biphenylenediamine derivative and a layer of a substance which has conventionally been used as a material of a hole transporting layer of an organic EL device. The hole transporting layer may also have a single layer structure consisting of, or a multi-layer structure comprising, a layer of a mixture of the p-phenylenediamine derivative or the 4,4'-biphenylenediamine derivative and a substance which has conventionally been used as a material of a hole transporting layer of an organic EL device. The preferable layer structures among these structures are the single layer structure consisting of a layer of the p-phenylenediamine derivative or the 4,4'-biphenylenediamine derivative, and a multi-layer structure comprising a layer of the p-phenylenediamine derivative or a layer of the 4,4'-biphenylenediamine derivative and a layer of a porphylin compound (such as a compound disclosed in Japanese Patent Application Laid-Open No. Showa 63(1988)295695, or the like), or a layer of an organic semi-conductive oligomer.

Typical examples of the porphylin compound include porphin, 5,10,15,20-tetraphenyl-21H-,23H-porphin copper (II), 5,10,15,20-tetraphenyl-21H-,23H-porphin zinc (II), 5,10,15,20-tetrakis(perfluorophenyl)-21H-,23H-porphin, silicon phthalocyanine oxide, aluminum phthalocyanine chloride, phthalocyanine (no metal), dilithium phthalocyanine, copper tetramethylphthalocyanine, copper phthalocyanine, chromium phthalocyanine, zinc phthalocyanine, lead phthalocyanine, titanium phthalocyanine oxide, magnesium phthalocyanine, copper octamethylphthalocyanine, and the like.

As the organic semi-conductive oligomer described above, a compound represented by the general formula (XV):

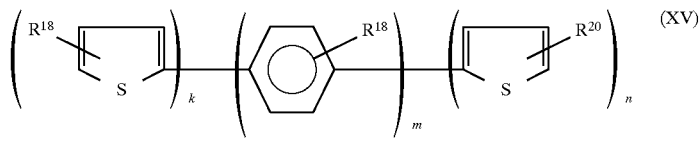

wherein $R^{18}$, $R^{19}$, and $R^{20}$ represent each an alkyl group having 1 to 10 carbon atoms, an alkoxy group having 1 to 10 carbon atoms, or cyclohexyl group, and may be the same with each other or different from each other, k, m, and n represent each an integer of 1 to 3, and the sum of k, m, and n is 5 or less, is particularly preferable.

In the electron injecting layer (the electron injecting and transporting layer) formed in the organic EL device of the present invention if necessary, any type of compound can be selected from conventional electron transporting compounds and used as the material of the electron injecting layer as long as the layer has the function of transporting the electron injected from the cathode to the organic light emitting layer.

Examples of the preferable electron transporting compound include compounds having the following formulae:

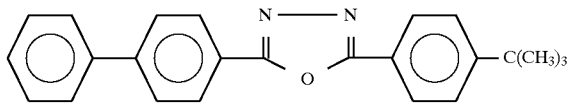

(98)

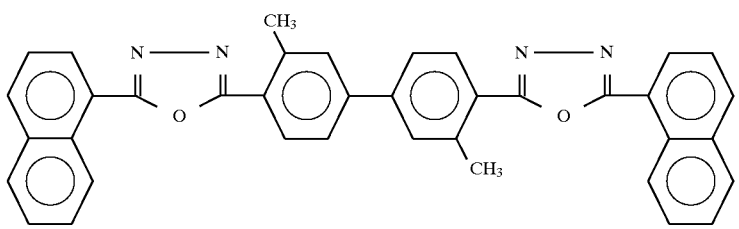

(99)

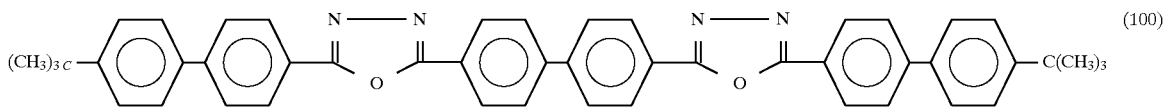

(100)

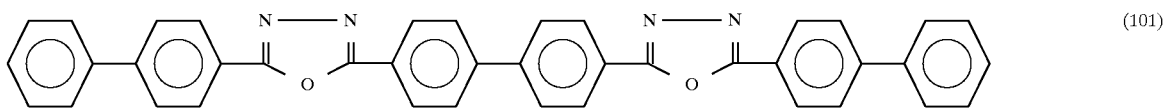

(101)

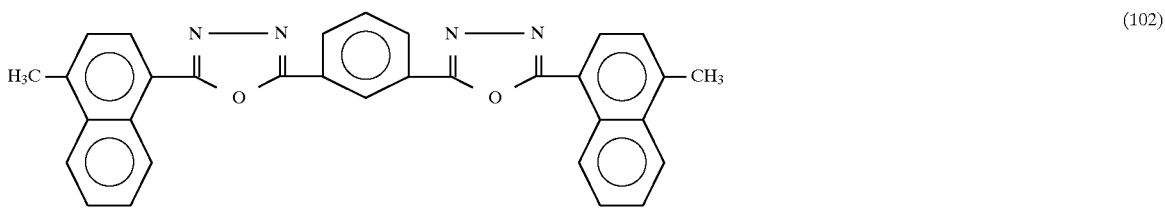

(102)

The electron injecting layer is the layer having any of the electron injecting property, the electron transporting property, and the electron barrier property, and the compounds (98) to (102) described above as well as crystalline or amorphous materials derived from Si, SiC, CdS, or the like, may be used for forming the layer.

The organic EL device of the present invention may also have a layer for improving adhesion between the layers in addition to the anode, the cathode, the organic light emitting layer, the hole transporting layer formed if necessary, and the electron injecting layer formed if necessary. Specific examples of the material used for such a layer, for example a layer for improving adhesion between the organic light emitting layer and the cathode, include metal complex compounds derived from quinolinol, such as tris(8-quinolinol)aluminum, tris(8-quinolinol)indium, and the like.

The organic EL device of the present invention described above can be produced by a process such as one of the following processes in accordance with the construction of the device.

(a) Preparation of an organic EL device having the construction of an anode/an organic light emitting layer (containing the p-phenylenediamine derivative or the 4,4'-biphenylenediamine derivative)/a cathode-1-.

An anode is prepared on a suitable substrate by forming a thin layer made of a desired electrode material, such as an anode material, in such a manner that the thickness of the layer is 1 $\mu$m or less, preferably in the range of 10 to 200 nm, by a method, such as the vapor deposition method, the sputtering method, or the like. Then, an organic light emitting layer is formed on the anode thus prepared by forming a thin layer of the p-phenylenediamine derivative or the 4,4'-biphenylenediamine derivative. The formation of the thin layer of the p-phenylenediamine derivative or the 4,4'-biphenylenediamine derivative can be conducted by a method, such as the vacuum vapor deposition method, the spin coating method, the casting method, or the like. Among these methods, the vacuum vapor deposition method is preferable because a uniform thin film is more easily obtained and possibility of formation of pin-holes is smaller.

When the vacuum vapor deposition method is conducted for forming a thin layer of the p-phenylenediamine derivative or the 4,4'-biphenylenediamine derivative, the conditions of the vacuum vapor deposition are varied depending on the type of the p-phenylenediamine derivative or the 4,4'-biphenylenediamine derivative, and the crystal structure and the association structure of the organic light emitting layer which is to be formed. It is generally preferred that the heating temperature of a boat is suitably selected in the range of 50° to 400° C., the degree of vacuum is suitably selected in the range of $10^{-6}$ to $10^{-3}$ Pa, the rate of vapor deposition is suitably selected in the range of 0.01 to 50 nm/sec, the temperature of the substrate is suitably selected in the range of −50° to +300° C., and the thickness of the film is suitably selected in the range of 5 nm to 5 $\mu$m.

After the organic light emitting layer is formed as described above, a cathode is prepared on the organic light emitting layer thus formed by forming a thin layer made of a material of the cathode in such a manner that the thickness of the layer is 1 $\mu$m or less, preferably in the range of 10 to 200 nm, by a method, such as the vapor deposition method, the sputtering method, or the like. The desired organic EL device can be obtained by the process described above. It is possible in this process for preparation of the organic EL device that the order of the preparation of layers is reversed, and a cathode, an organic light emitting layer, and an anode are formed on a substrate in this order.

(b) Preparation of an organic EL device having the construction of an anode/an organic light emitting layer (containing the p-phenylenediamine derivative or the 4,4'-biphenylenediamine derivative)/a cathode-2-.

An anode is prepared on a suitable substrate by the same procedures as those used in (a) described above. Then, an organic light emitting layer is formed on the anode thus prepared by coating the anode with a solution containing a material of the hole transporting layer, a material of the organic light emitting layer, a material of the electron injecting layer, a binder (polyvinylcarbozole or the like), and the like materials.

Subsequently, a cathode is prepared by forming a thin layer made of a material of the cathode on the organic light emitting layer by the same procedures as those used in (a) described above. The desired organic EL device can be obtained by the process described above.

An organic light emitting layer having a multi-layer structure may be prepared by forming a layer of a thin layer of a desired material of the organic light emitting layer on the layer formed in the above by a method, such as the vapor deposition method. The organic light emitting layer may also be formed by simultaneous vapor deposition of the material of the organic light emitting layer, the material of the hole transporting layer, and the material of the electron injecting layer.

(c) Preparation of an organic EL device having the construction of an anode/a hole transporting layer (containing the p-phenylenediamine derivative or the 4,4'-biphenylenediamine derivative)/an organic light emitting layer/a cathode.

An anode is prepared on a suitable substrate by the same procedures as those used in (a) described above. A hole transporting layer is formed on the anode thus prepared by forming a thin layer of the p-phenylenediamine derivative or the 4,4'-biphenylenediamine derivative. The formation of the hole transporting layer can be conducted by the same procedures as those used in the formation of the organic light emitting layer (containing the p-phenylenediamine derivative or the 4,4'-biphenylenediamine derivative) in (a) described above.

Then, an organic light emitting layer is formed on the hole transporting layer by using a desired material of the organic light emitting layer. The organic light emitting layer can be formed by preparing a thin layer of the material of the light emitting layer using a method, such as the vacuum vapor deposition method, the spin coating method, the casting method, or the like. Among these methods, the vacuum vapor deposition method is preferable because a uniform thin layer is more easily obtained and possibility of formation of pin-holes is smaller. Subsequently, a cathode is prepared by forming a thin layer made of a material of the cathode on the organic light emitting layer by the same procedures as those used in (a) described above. The desired organic EL device can be obtained by the process described above. It is possible also in this process for preparation of the organic EL device that the order of the preparation of the layers is reversed, and an anode, a cathode, an organic light emitting layer, a hole transporting layer, and an anode are prepared on a substrate in this order.

(d) Preparation of an organic EL device having the construction of an anode/a hole transporting layer (containing the p-phenylenediamine derivative or the 4,4'-biphenylenediamine derivative)/an organic light emitting layer/an electron injecting layer/a cathode.

An anode, a hole transporting layer (containing the p-phenylenediamine derivative or the 4,4'-biphenylenediamine derivative), and an organic light emitting layer are formed on a suitable substrate by the same procedures as those used in (c).

After the organic light emitting layer is formed, an electron injecting layer is formed by forming a thin layer made of an electron transporting compound on the organic light emitting layer in such a manner that the thickness of the layer is 1 μm or less, preferably in the range of 5 to 100 nm, by a method, such as the vapor deposition method, the sputtering method, or the like. Subsequently, a cathode is prepared by forming a thin layer made of a material of the cathode on the prepared electron injecting layer by the same procedures as those used in (c) described above. The desired organic EL device can be prepared by the process described above. It is possible also in this process for preparation of the organic EL device that the order of the preparation of layers is reversed, and a cathode, an electron injecting layer, an organic light emitting layer, a hole transporting layer, and an anode are formed on a substrate in this order.

The organic EL device of the present invention which can be prepared as described above emits light by applying a direct voltage of 5 to 40 V in the condition that the anode is connected to a positive electrode (+) and the cathode is connected to a negative electrode (−). When the connection is reversed, no electric current is observed and no light is emitted at all. When an alternating voltage is applied to the organic EL device, light emission is observed only in the condition that the polarity of the anode is positive and the polarity of the cathode is negative. When an alternating voltage is applied to the organic EL device, any type of wave shape can be used.

The organic EL device of the present invention is an organic EL device in which at least one of the layers of compound, which have a single layer structure or a multi-layer structure and at least contain an organic light emitting layer, contains a p-phenylenediamine derivative having 6 or more benzene ring skeletons, or an organic EL device in which at least one of the layers of compound, which have a single layer structure or a multi-layer structure and at least contain an organic light emitting layer, contains the 4,4'-biphenylenediamine derivative having 5 or more biphenyl group. The organic EL device has an improved life of light emission and very excellent durability The present invention is described in more detail in the following with reference to examples. However, the present invention is not limited by the examples.

PREPARATION EXAMPLE 1

A 300 ml flask of an egg-plant shape was charged with 3.42 g (13.2 mmol) of N,N'-diphenyl-1,4-phenylenediamine [a product of Kanto Kagaku Co., Ltd.], 9.35 g (33.4 mmol) of 4-iododiphenyl [a product of Nard Kenkyusho], 5.22 g (37.8 mmol) of anhydrous calcium carbonate, and 1 g (16 mmol) of copper powder. In the flask, the mixture was suspended in 300 ml of dimethylsulfoxide (DMSO), and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator. The obtained compound was purified by using a column packed with Wakogel C-200 (a product of Hiroshima Wako Co., Ltd.) with toluene used as the developing solvent, to obtain 2.53 g of a light yellow powder.

When this product was analyzed by the IR spectroscopy, absorptions were found at 3500, 3050, 1610, 1520, 1500, 1330, 1300, 1280, 850, 770, 710, and 540 cm$^{-1}$. When this product was analyzed by the FD-MS (the field diffusion mass spectroscopy), a peak at m/z=564 which corresponds to $C_{42}H_{32}N_2$=564 was observed. Therefore, the product was identified to be N,N'-bis-(4-biphenyl)-N,N'-diphenyl-1,4-phenylenediamine [Compound (1)]. The yield was 34%, and the melting point was 211° to 213° C.

PREPARATION EXAMPLE 2

A 300 ml flask of an egg-plant shape was charged with 5.02 g (13.9 mmol) of N,N'-di-(2-naphthyl)-1,4-phenylenediamine [a product of Kanto Kagaku Co., Ltd.], 8.25 g (40.4 mmol) of 4-iodobenzene [a product of Tokyo Kasei Co., Ltd.], 6.84 g (49.6 mmol) of anhydrous calcium carbonate, and 1 g (16 mmol) of copper powder. In the flask, the mixture was suspended in 300 ml of DMSO, and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator. The obtained compound was purified by using a column packed with Wakogel C-200 (a product of Hiroshima Wako Co., Ltd.) with toluene used as the developing solvent, to obtain 2.95 g of a light yellow powder.

When this product was analyzed by the IR spectroscopy, absorptions were found at 3450, 3050, 1640, 1600, 1510, 1480, 1280, 750, and 700 $cm^{-1}$. When this product was analyzed by the FD-MS, a peak at m/z=512 which corresponds to $C_{38}H_{28}N_2$=512 was observed. Therefore, the product was identified to be N,N'-di-(2-naphthyl)-N,N'-diphenyl-1,4-phenylenediamine [Compound (2)]. The yield was 41%, and the melting point was 190° to 193° C.

PREPARATION EXAMPLE 3

A 300 ml flask of an egg-plant shape was charged with 2.13 g (5.92 mmol) of N,N'-di-(2-naphthyl)-1,4-phenylenediamine [a product of Kanto Kagaku Co., Ltd.], 4.70 g (16.8 mmol) of 4-iododiphenyl [a product of Nard Kenkyusho], 3.19 g (23.3 mmol) of anhydrous calcium carbonate, and 1 g (16 mmol) of copper powder. In the flask, the mixture was suspended in 300 ml of DMSO, and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator. The obtained compound was purified by using a column packed with Wakogel C-200 (a product of Hiroshima Wako Co., Ltd.) with toluene used as the developing solvent, to obtain 1.55 g of a light yellow powder.

When this product was analyzed by the IR spectroscopy, absorptions were found at 3480, 3060, 1640, 1610, 1510, 1500, 1480, 1290, 1280, 770, 760, and 700 $cm^{-1}$. When this product was analyzed by the FD-MS, a peak at m/z=664 which corresponds to $C_{50}H_{36}N_2$=664 was observed. Therefore, the product was identified to be N,N'-di-(2-naphthyl)-N,N'-di-(4-biphenyl)-1,4-phenylenediamine [Compound (3)]. The yield was 39%, and the melting point was 252° to 253° C.

PREPARATION EXAMPLE 4

A 300 ml flask of an egg-plant shape was charged with 1.00 g (9.26 mmol) of 1,4-phenylenediamine [a product of Tokyo Kasei Co., Ltd.], 11.0 g (39.3 mmol) of 4-iododiphenyl [a product of Nard Kenkyusho], 12.2 g (88.4 mmol) of anhydrous calcium carbonate, and 1 g (16 mmol) of copper powder. In the flask, the mixture was suspended in 200 ml of dimethylsulfoxide (DMSO), and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator. The obtained compound was purified by using a column packed with Wakogel C-200 (a product of Hiroshima Wako Co., Ltd.) with toluene used as the developing solvent, to obtain 1.4 g of a light yellow powder.

When this product was analyzed by the IR spectroscopy, absorptions were found at 3500, 3080, 1620, 1530, 1510, 1340, 1300, 1280, 850, 780, and 710 $cm^{-1}$. When this product was analyzed by the FD-MS, a peak at m/z=716 which corresponds to $C_{54}H_{40}N_2$=716 was observed. $^1$HNMR of the product was also measured (1,4-dioxane). The obtained NMR spectrum is shown in FIG. 1.

From these results, the product was identified to be N,N,N',N'-tetrakis-(4-biphenyl)-1,4-phenylenediamine [Compound (27)]. The yield was 20%, and the melting point was 310° C.

PREPARATION EXAMPLE 5

A 300 ml flask of an egg-plant shape was charged with 0.50 g (4.63 mmol) of 1,4-phenylenediamine [a product of Tokyo Kasei Co., Ltd.], 6.68 g (22.7 mmol) of 4-methyl-4-iododiphenyl [a product of Nard Kenkyusho], 5 g (36 mmol) of anhydrous calcium carbonate, and 1 g (16 mol) of copper powder. In the flask, the mixture was suspended in 200 ml of DMSO, and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator. The obtained compound was purified by using a column packed with Wakogel C-200 (a product of Hiroshima Wako Co., Ltd.) with toluene used as the developing solvent, to obtain 0.40 g of a light yellow powder.

Figure 2:
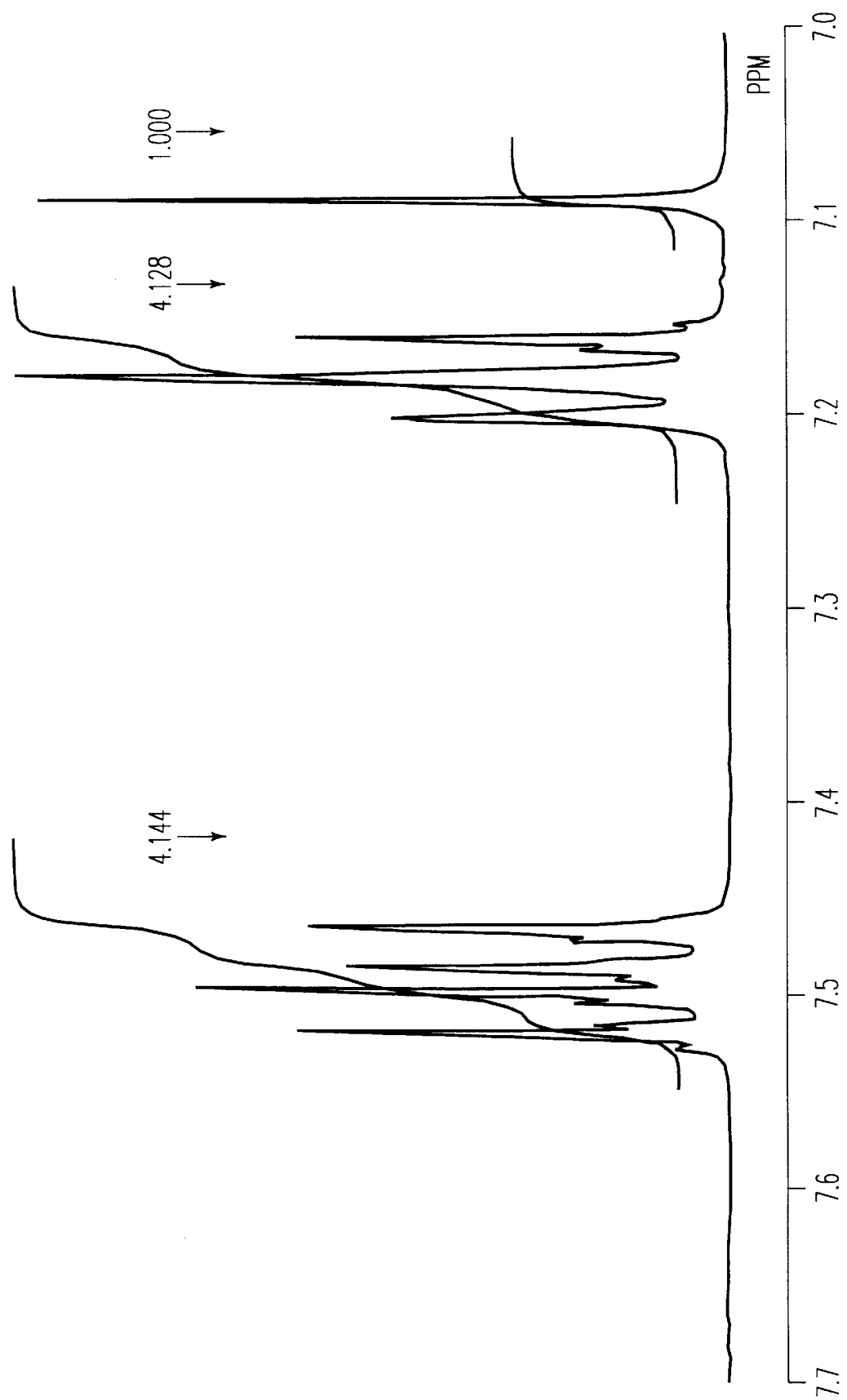

When this product was analyzed by the IR spectroscopy, absorptions were found at 3500, 3060, 1600, 1530, 1490, 1300, 840, 770, and 710 $cm^{-1}$. When this product was analyzed by the FD-MS, a peak at m/z=772 which corresponds to $C_{58}H_{48}N_2$=772 was observed. $^1$H-NMR of the product was also measured (1,4-dioxane). The obtained NMR spectrum is shown in FIG. 2.

From these results, the product was identified to be N,N,N',N'-tetrakis-(4'-methyl-4-biphenyl)-1,4-phenylenediamine[Compound (28)]. The yield was 10%, and the melting point was 295° C.

PREPARATION EXAMPLE 6

A 300 ml flask of an egg-plant shape was charged with 5.03 g (18.8 mmol) of N,N'-diacetyl-4,4'-benzidine [a product of Tokyo Kasei Co., Ltd.], 12.3 g (43.8mmol) of 4-iododiphenyl, 11 g (80 mmol) of anhydrous calcium carbonate, and 1 g (16 mmol) of copper powder. In the flask, the mixture was suspended in 200 ml of DMSO, and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator.

The remaining product was dissolved in 500 ml of tetrahydrofuran (THF), and 50 ml of an aqueous solution prepared by dissolving 20 g of potassium hydroxide and 300 of ethanol were added to the THF solution. The hydrolysis was allowed to proceed by heating the solution for 5 hours under stirring in a 1 liter flask. The reaction product was extracted with ethyl acetate, and the extract was dried with anhydrous sodium sulfate. The obtained compound was purified by using a column packed with Wakogel C-200 (a product of Hiroshima Wako Co., Ltd.) with methylene chloride used as the developing solvent, to obtain 9.3 g of an intermediate product as an ocher powder.

A 300 ml three-necked flask was charged with 1.02 g (2.09 mmol) of the intermediate product, 1.54 g (5.50 mmol) of 4-iododiphenyl, 1.99 g (14.4 mmol) of anhydrous potassium carbonate, and 1 g (16 mmol) of copper powder. In the flask, the mixture was suspended in 200 ml of DMSO, and was allowed to react at 180° C. for 5 hours. Then, inorganic components were removed by filtration, and the filtrate was extracted with methylene chloride. The extract was dried with anhydrous sodium sulfate, and the solvent was removed in a vacuum from the dried extract by using an evaporator. The obtained compound was purified by using a column packed with Wakogel C-200 (a product of Hiroshima Wako Co., Ltd.) with toluene used as the developing solvent, to obtain 0.50 g of a light yellow powder.

Figure 3A:
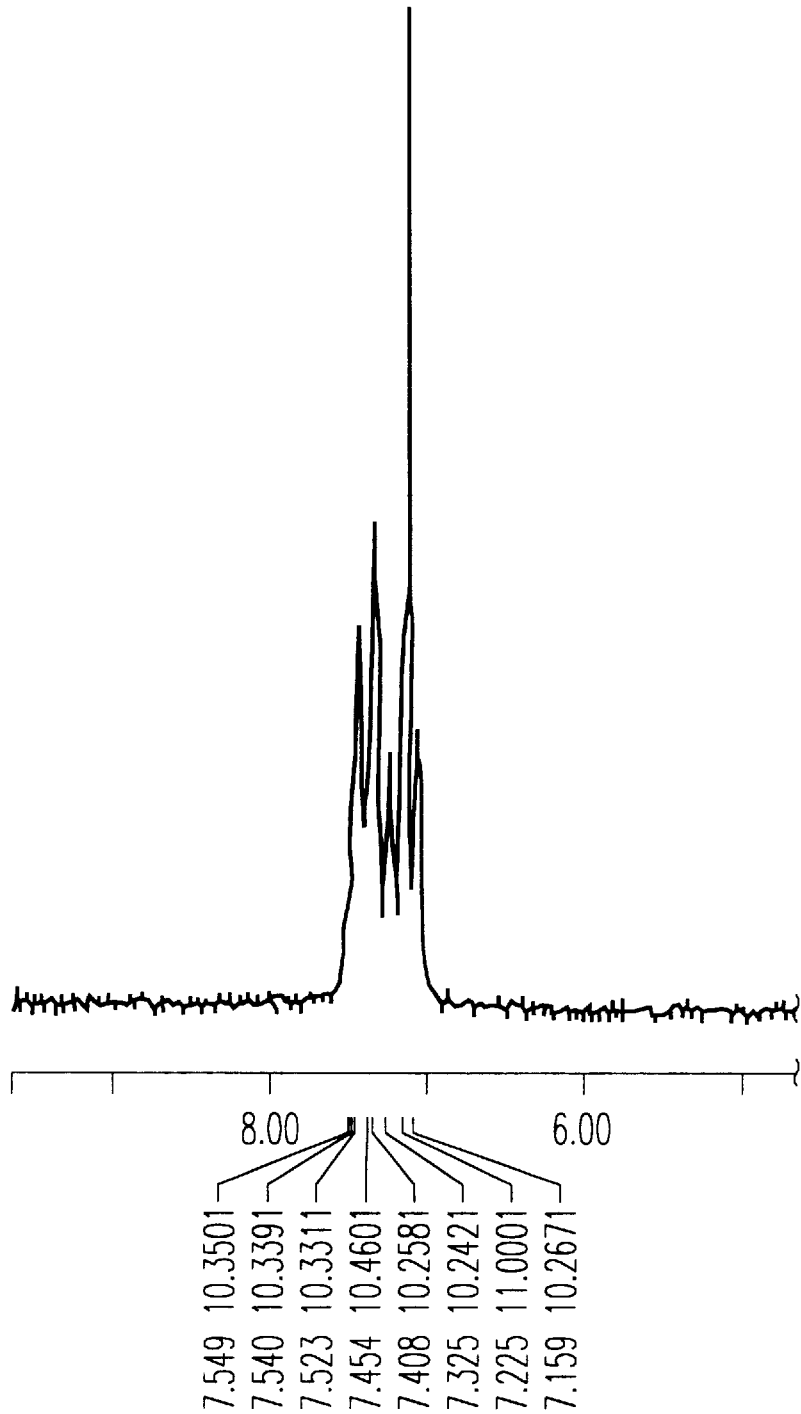
Figure 3B:
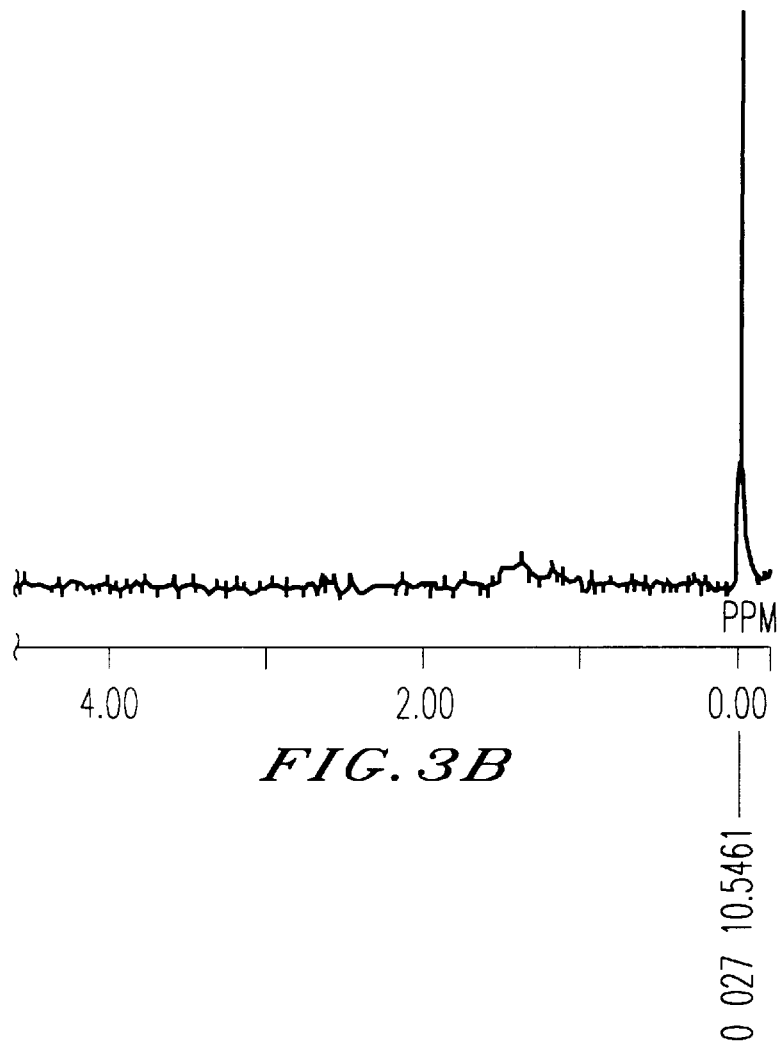

When this product was analyzed by the IR spectroscopy, absorptions were found at 3490, 3050, 1610, 1500, 1430, 1300, 850, 770, and 710 cm$^{-1}$. When this product was analyzed by the FD-MS, a peak at m/z=792 which corresponds to $C_{60}H_{44}N_2$=792 was observed. $^1$H-NMR of the product was also measured (solvent, deuterated chloroform; reference substance, tetramethylsilane (TMS)). The obtained NMR spectrum is shown in FIG. 3.

From these results, the light yellow powder was identified to be N,N,N',N'-tetrakis-(4-biphenyl)-4,4'-benzidine [Compound (61)]. The yield was 20%, and the melting point was 265° C.

PREPARATION EXAMPLE 7

The intermediate product prepared in Preparation Example 6 in an amount of 1.03 g (2.12 mmol), 2.02 g (6.87 mmol) of 4'-methyl-4-iododiphenyl, 2.00 g of (14.6 mmol) of anhydrous potassium carbonate, and 1 g (16 mmol) of copper powder were allowed to react in accordance with the same procedures as those used in Preparation Example 6, to obtain 0.47 g of a light yellow powder.

Figure 4A:
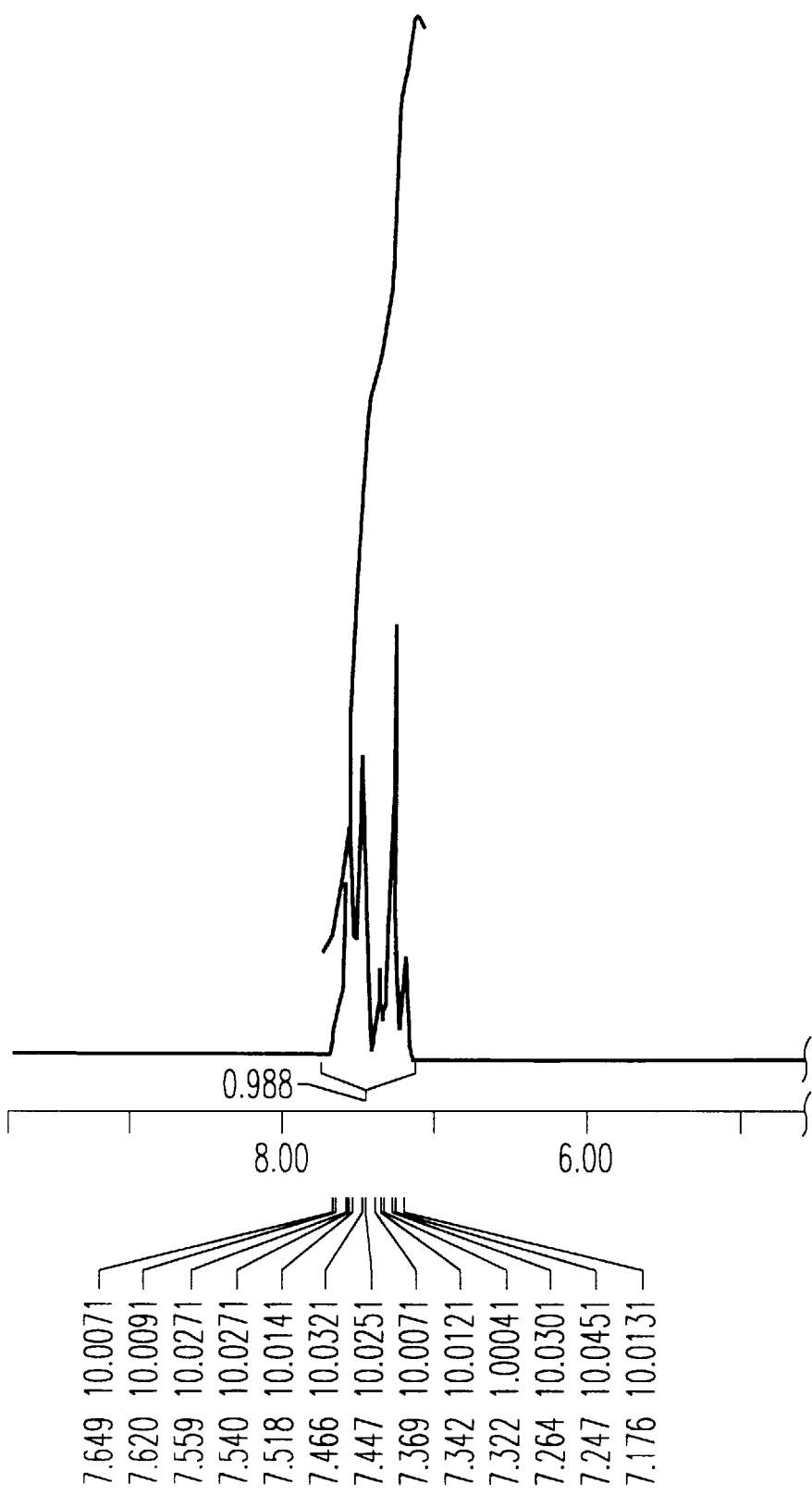
Figure 4B:
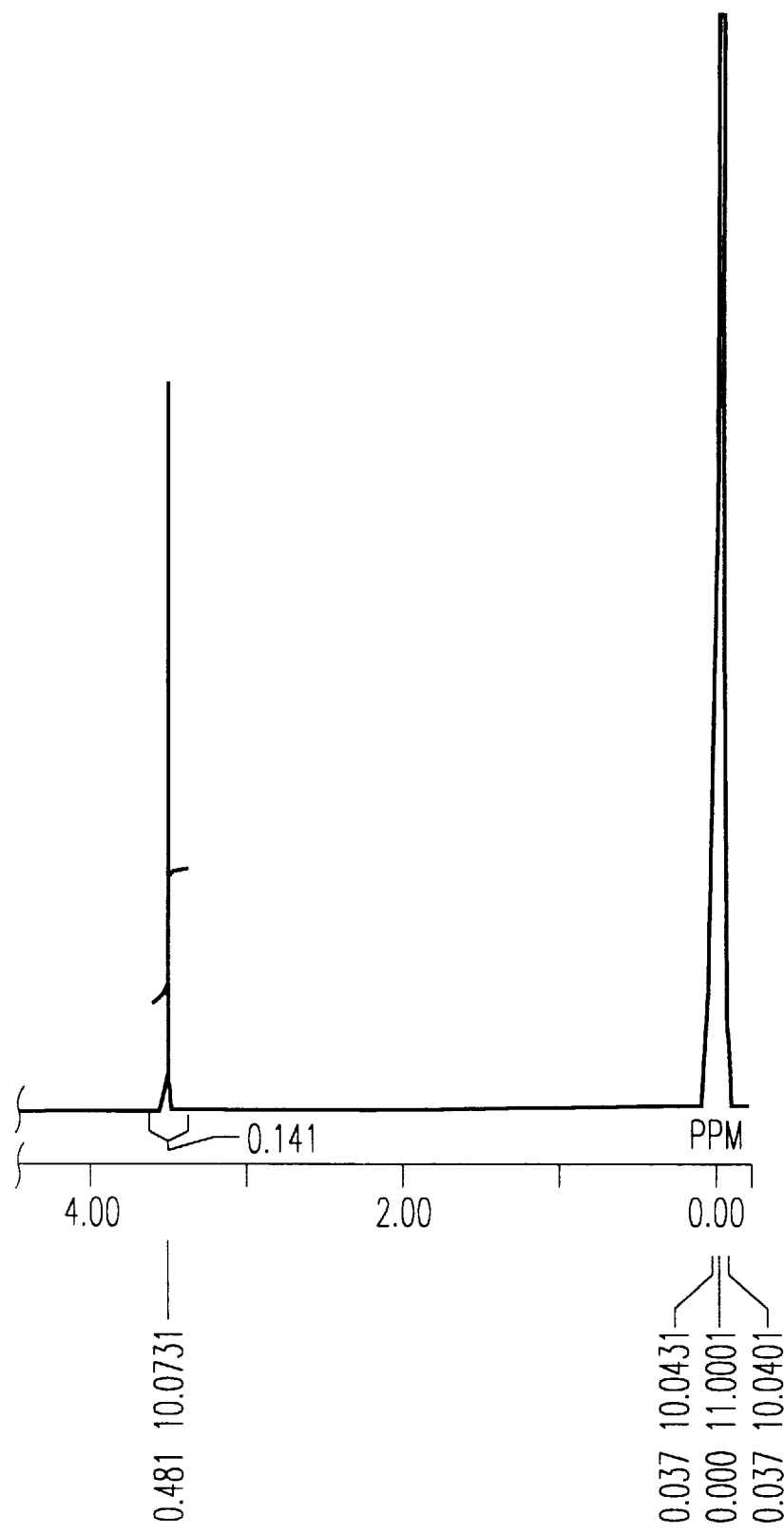

When this product was analyzed by the IR spectroscopy, absorptions were found at 3490, 3060, 1600, 1500, 1420, 1290, 850, 770, and 710 cm$^{-1}$. When this product was analyzed by the FD-MS, a peak at m/z=820 which corresponds to $C_{62}H_{48}N_2$=820 was observed. $^1$H-NMR of the product was also measured (solvent, deuterated chloroform; reference substance, tetramethylsilane (TMS)). The obtained NMR spectrum is shown in FIG. 4.

From these results, the light yellow powder was identified to be N,N'-bis-(4-biphenyl)-N,N'-bis(4'-methyl-4-biphenyl) -4,4'-benzidine [Compound (62)]. The yield was 27%, and the melting point was 257° C.

EXAMPLE 1

A coated plate prepared by coating an ITO electrode on a glass substrate of 25 mm×75 mm×1.1 mm to the thickness of 100 nm was used as the transparent supporting substrate. The prepared transparent supporting substrate was cleaned with isopropyl alcohol under ultrasonic wave.

The cleaned supporting substrate was fixed to a substrate holder of a vacuum vapor deposition system [a product of Nippon Shinku Gijutsu Co., Ltd.]. In an electrically heated boat made of molybdenum, 200 mg of tris(3-methylphenylphenylamino)triphenylamine (MTDATA) was placed, and 200 mg of Compound (1) obtained in Preparation Example 1 was placed in another electrically heated boat made of molybdenum. In still another electrically heated boat made of molybdenum, 200 mg of 4,4'-bis(2,2-diphenylvinyl)biphenyl (DPVBi) was placed.

After the pressure in a vacuum chamber was decreased to 1×10$^{-4}$ Pa, the boat containing MTDATA was heated, and a film of MTDATA was prepared on the ITO electrode to the thickness of 60 nm at a rate of 0.1 to 0.3 nm/sec. Then, the boat containing Compound (1) was heated, and a hole transporting layer of 20 nm thickness was prepared by accumulating Compound (1) at a rate of vapor deposition of 0.1 to 0.3 nm/sec. Subsequently, DPVBi was laminated on the prepared hole transporting layer to the thickness of 40 nm by vapor deposition from still another boat to prepare a light emitting layer. The rate of vapor deposition was 0.1 to 0.2 nm/min.

Then, the pressure in the vacuum chamber was brought to an atmospheric pressure, and an electrically heated boat made of molybdenum which was newly charged with 100 mg of tris(8-quinolinol)aluminum (Alq) was attached to the vacuum vapor deposition system, and the pressure in the vacuum chamber was then decreased to 1×10$^{-4}$ Pa. From this boat, Alq (an electron injecting layer) was accumulated to the thickness of 20 nm at a rate of 0.1 to 0.2 nm/sec.

As the last step, the obtained plate was taken out from the vacuum chamber, and after placing a mask made of stainless steel on the above-obtained injection layer, the plate was again fixed to the substrate holder. In a tungsten basket, 0.5 g of silver wire was placed, and 1 g of magnesium ribbon was placed in a boat of molybdenum. The pressure in the vacuum chamber was decreased to 1×10$^{-4}$ Pa, and magnesium and silver were simultaneously vapor deposited at the rates of 1.8 nm/sec and 0.1 nm/sec, respectively, to prepare a cathode.

EXAMPLE 2

A device was prepared by the same procedures as those used in Example 1 except that Compound (2) obtained in Preparation Example 2 was used as the material of the hole transporting layer in place of Compound (1) obtained in Preparation Example 1 which was used in Example 1.

EXAMPLE 3

A device was prepared by the same procedures as those used in Example 1 except that Compound (3) obtained in Preparation Example 3 was used as the material of the hole transporting layer in place of Compound (1) obtained in Preparation Example 1 which was used in Example 1.

EXAMPLE 4

A device was prepared by the same procedures as those used in Example 1 except that Compound (27) obtained in Preparation Example 4 was used as the material of the hole transporting layer in place of Compound (1) obtained in Preparation Example 1 which was used in Example 1.

EXAMPLE 5

A device was prepared by the same procedures as those used in Example 1 except that Compound (28) obtained in Preparation Example 5 was used as the material of the hole transporting layer in place of Compound (1) obtained in Preparation Example 1 which was used in Example 1.

EXAMPLE 6

A device was prepared by the same procedures as those used in Example 1 except that Compound (61) obtained in Preparation Example 6 was used as the material of the hole transporting layer in place of Compound (1) obtained in Preparation Example 1 which was used in Example 1.

EXAMPLE 7

A device was prepared by the same procedures as those used in Example 1 except that Compound (62) obtained in Preparation Example 7 was used as the material of the hole transporting layer in place of Compound (1) obtained in Preparation Example 1 which was used in Example 1.

COMPARATIVE EXAMPLE 1

A device was prepared by the same procedures as those used in Example 1 except that N,N'-diphenyl-N,N'-bis(3-methylphenyl)-1,1'biphenyl-4,4'-diamine (TPD) was used as the material of the hole transporting layer in place of Compound (1) obtained in Preparation Example 1 which was used in Example 1.

COMPARATIVE EXAMPLE 2

A device was prepared by the same procedures as those used in Example 1 except that N,N,N',N'-tetraphenyl-p-phenylenediamine was used as the material of the hole transporting layer in place of Compound (1) obtained in Preparation Example 1 which was used in Example 1.

COMPARATIVE EXAMPLE 3

A device was prepared by the same procedures as those used in Example 1 except that N,N,N',N'-tetrakis-(4-biphenyl)-m-phenylenediamine was used as the material of the hole transporting layer in place of Compound (1) obtained in Preparation Example 1 which was used in Example 1.

COMPARATIVE EXAMPLE 4

A device was prepared by the same procedures as those used in Example 1 except that N,N,N',N'-tetrakis-(4-biphenyl)-3,3'-dimethyl-4,4'-benzidine was used as the material of the hole transporting layer in place of Compound (1) obtained in Preparation Example 1 which was used in Example 1.

The lives of light emission of the devices obtained in Examples 1 to 7 and Comparative Example 1 to 4 are shown in Table 1.

The life of light emission is the time passed for each device from the start of light emission with the initial luminance of 100 cd/m$^2$ to the time when the luminance decreased to 50 cd/m$^2$ which is a half of the initial value, while the device is driven by a constant current.

The devices of Examples 1 to 7 had very remarkably improved lives of light emission in comparison with that of the device using TPD (Comparative Example 1) which is the hole transporting material showing the longest life of light emission among conventional materials.

N,N,N',N'-Tetraphenyl-p-phenylenediamine used in Comparative Example 2 is a conventional hole transporting material. This material has high crystallizability because this material has only 5 benzene rings in the molecule, and dielectric breakdown occurred during the measurement of the life of light emission. In contrast, compounds used in Examples 1 to 7 did not show crystallization at all because they all have 6 or more benzene rings in the molecule, and uniform films could be maintained for a long time.

N,N,N',N'-Tetrakis-(4-biphenyl)-m-phenylenediamine used in Comparative Example 3 also has 6 or more benzene rings in the molecule, and no problem arose with respect to formation and maintenance of a thin layer. However, the life of light emission was found to be very short.

N,N,N',N'-Tetrakis-(4-biphenyl)-3,3'-dimethyl-4,4'-benzidine used in Comparative Example 4 also has 6 or more benzene rings in the molecule, and no problem arose with respect to formation and maintenance of a thin layer. However, the life of light emission was found to be very short.

TABLE 1

| | hole transporting material | life of light emission |
|---|---|---|
| Example 1 | Compound (1) | 220 hours |
| Example 2 | Compound (2) | 180 hours |
| Example 3 | Compound (3) | 230 hours |
| Example 4 | Compound (27) | 350 hours |
| Example 5 | Compound (28) | 350 hours |
| Example 6 | Compound (61) | 160 hours |
| Example 7 | Compound (62) | 180 hours |
| Comparative Example 1 | N,N'-diphenyl-N,N'-bis(3-methylphenyl)-1,1'-biphenyl-4,4'-diamine | 70 hours |
| Comparative Example 2 | N,N,N',N'-tetraphenyl-p-phenylenediamine | dielectric breakdown after 12 hours |
| Comparative Example 3 | N,N,N',N'-tetrakis-(4-biphenyl)-m-phenylene-diamine | 10 hours |
| Comparative Example 4 | N,N,N',N'-tetrakis(4-biphenyl)-3,3'-dimethyl-4,4'-benzidine | 11 hours |

INDUSTRIAL APPLICABILITY

The organic EL device of the present invention contains a p-phenylenediamine derivative or a 4,4'-biphenylenediamine derivative as a component thereof, and has the characteristics that the life of light emission is improved and that the durability is excellent.

The arylenediamine derivative of the present invention can remarkably improve the life of light emission of an organic EL device.

I claim:

1. An organic electroluminescence device at least containing a p-phenylenediamine derivative having 6 or more benzene ring skeletons which is represented by the general formula (I):

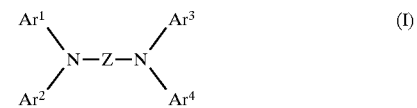

wherein Z represents p-phenylene group; $Ar^1$, $Ar^2$, $Ar^3$, and $Ar^4$ represent each an aryl group having 6 to 20 carbon atoms, and may be the same with each other or different from each other; Z, $Ar^1$, $Ar^2$, $Ar^3$, and $Ar^4$ may each be substituted with alkyl groups having 1 to 6 carbon atoms, alkoxy groups having 1 to 6 carbon atoms, or phenyl groups; and the combination of $Ar^1$, $Ar^2$, $Ar^3$, $Ar^4$, and Z of the central skeleton must have 6 or more benzene ring skeletons.

2. An organic electroluminescence device according to claim 1, wherein the p-phenylenediamine derivative represented by the general formula (I) is used as a material of a hole transporting layer.

3. An organic electroluminescence device according to claim 1, wherein $Ar^1$, $Ar^2$, $Ar^3$, and $Ar^4$ in the general formula (I) representing the p-phenylenediamine derivative are each a group at least having naphthyl group or biphenyl group.

4. A p-phenylenediamine derivative represented by the general formula (II):

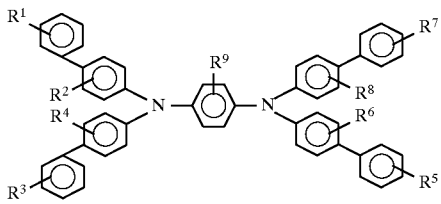

(II)

wherein $R^1$ to $R^9$ represent each a hydrogen atom, an alkyl group having 1 to 6 carbon atoms, an alkoxy group having 1 to 6 carbon atoms, or a phenyl group, and may be the same with each other or different from each other; and $R^1$ and $R^2$, $R^2$ and $R^4$, $R^3$ and $R^4$, $R^5$ and $R^6$, $R^6$ and $R^8$, $R^7$ and $R^8$, $R^2$ and $R^9$, $R^4$ and $R^9$, $R^6$ and $R^9$, and $R^8$ and $R^9$, may each form a ring by being bonded to each other.

5. An organic electroluminescence device at least containing the p-phenylene diamine derivative represented by the general formula:

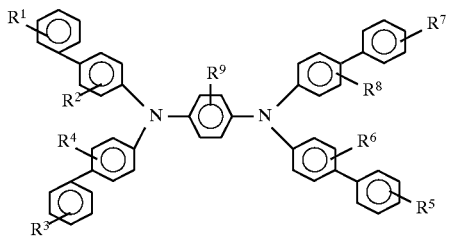

(II)

wherein $R^1$ to $R^9$ represent each a hydrogen atom an alkyl group having 1 to 6 carbon atoms, an alkoxy group having 1 to 6 carbon atoms, or a phenyl group, and may be the same with each other or different from each other; and $R^1$ and $R^2$, $R^2$ and $R^4$, $R^3$ and $R^4$, $R^5$ and $R^6$, $R^6$ and $R^8$, $R^7$ and $R^8$, $R^2$ and $R^9$, $R^4$ and $R^9$, $R^6$ and $R^9$, and $R^8$ and $R^9$, may each form a ring by being bonded to each other.

6. An organic electroluminescence device according to claim 5, wherein the p-phenylenediamine derivative represented by the general formula (II) is used as a material of a hole transporting layer.

7. A 4,4'-biphenylenediamine derivative represented by the general formula (III):

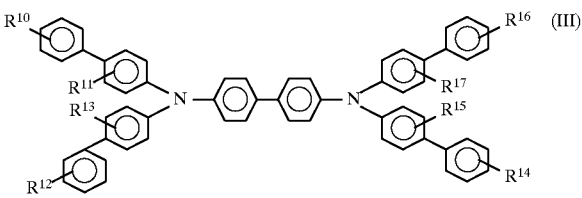

(III)

wherein $R^{10}$ to $R^{17}$ represent each a hydrogen atom, an alkyl group having 1 to 6 carbon atoms, an alkoxy group having 1 to 6 carbon atoms, or a phenyl group, and may be the same with each other or different from each other; and $R^{10}$ and $R^{11}$, $R^{11}$ and $R^{13}$, $R^{12}$ and $R^{13}$, $R^{14}$ and $R^{15}$, $R^{15}$ and $R^{17}$, and $R^{16}$ and $R^{17}$, may each form a ring by being bonded to each other.

8. An organic electroluminescence device at least containing the 4,4'-biphenylenediamine derivative represented by the general formula (III):

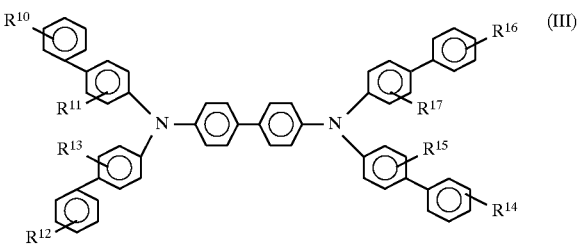

(III)

wherein $R^{10}$ to $R^{17}$ represent each a hydrogen atom, an alkyl group having 1 to 6 carbon atoms, an alkoxy group having 1 to 6 carbon atoms, or a phenyl group, and may be the same with each other or different from each other; and $R^{10}$ and $R^{11}$, $R^{11}$ and $R^{13}$, $R^{12}$ and $R^{13}$, $R^{14}$ and $R^{15}$, $R^{15}$ and $R^{17}$, and $R^{16}$ and $R^{17}$, may each form a ring by being bonded to each other.

9. An organic electroluminescence device according to claim 8, wherein the 4,4'-biphenylenediamine derivative represented by the general formula (III) is used as a material of a hole transporting layer.

* * * * *